(12) United States Patent
Shaw et al.

(10) Patent No.: US 7,118,552 B2
(45) Date of Patent: Oct. 10, 2006

(54) AUTOMATICALLY OPERABLE SAFETY SHIELD SYSTEM FOR SYRINGES

(75) Inventors: Derek J. Shaw, Macclesfield (GB); Brian R. Law, Leicester (GB)

(73) Assignee: AstraZeneca AB, Sodertalje (SE)

( * ) Notice: Subject to any disclaimer, the term of this patent is extended or adjusted under 35 U.S.C. 154(b) by 424 days.

(21) Appl. No.: 09/936,859

(22) PCT Filed: Feb. 13, 2001

(86) PCT No.: PCT/GB01/00590

§ 371 (c)(1),
(2), (4) Date: Nov. 15, 2001

(87) PCT Pub. No.: WO01/60435

PCT Pub. Date: Aug. 23, 2001

(65) Prior Publication Data

US 2002/0161337 A1 Oct. 31, 2002

(30) Foreign Application Priority Data

Feb. 18, 2000 (GB) .............................. 0003790

(51) Int. Cl.
*A61M 5/00* (2006.01)

(52) U.S. Cl. ........................ 604/110; 604/187; 604/198
(58) Field of Classification Search ................. 604/181, 604/110, 187, 188, 192, 197, 198, 263
See application file for complete search history.

(56) References Cited

U.S. PATENT DOCUMENTS

| 2,571,653 | A | 10/1951 | Bastein | 128/218 |
| 2,845,065 | A | 7/1958 | Gabriel | 128/215 |
| 2,925,083 | A | 2/1960 | Craig | 128/218 |

(Continued)

FOREIGN PATENT DOCUMENTS

| DE | 813 433 | 7/1949 |
| DE | 924 734 | 5/1963 |
| DE | 233 302 | 5/1971 |
| DE | 1 297 746 | 11/1972 |
| DE | 19755125 A1 | 6/1999 |
| EP | 0 307 367 | 3/1989 |
| EP | 0 405 039 | 1/1991 |
| EP | 0 467 173 | 1/1992 |
| EP | 0 307 367 B1 | 6/1992 |
| EP | 0 645 155 A2 | 9/1994 |
| EP | 0 740 942 | 8/1999 |
| EP | 0 966 983 A | 12/1999 |
| FR | 2 648 716 | 12/1990 |

(Continued)

OTHER PUBLICATIONS

Copy of IPEA Report for PCT/GB01/00590.

*Primary Examiner*—Jerome W. Donnelly
*Assistant Examiner*—Kevin C. Sirmons
(74) *Attorney, Agent, or Firm*—Fish & Richardson P.C.

(57) ABSTRACT

An automatically operable safety shield system for use with a syringe, the safety shield system including an holder having proximal and distal portions and defining an enclosure into which the syringe may be inserted, an outer shield having proximal and distal portions, mounted outwards from the inner holder being axially movable relative to the inner holder between retracted and extended positions, a spring positioned between a first detent on the inner holder and a second detent on the outer shield, and urging the outer shield to its extended position, the inner holder having at least one first opening and the outer shield having at least one first stop member, the first stop member being engageable with the first opening when the outer shield is in the retracted position, the inner holder having distal to the first opening at least one first indentation, the first stop member being engageable with the first indentation when the outer shield is in the extended position.

20 Claims, 25 Drawing Sheets

U.S. PATENT DOCUMENTS

| | | | | |
|---|---|---|---|---|
| 3,323,523 A | 6/1967 | Scislowicz | | 128/214.4 |
| 3,377,989 A | 4/1968 | Sandhage et al. | | 119/1 |
| 3,463,152 A | 8/1969 | Sorenson | | 128/214.4 |
| 3,536,073 A | 10/1970 | Farb | | 128/214.4 |
| 3,574,306 A | 4/1971 | Alden | | 128/214.4 |
| 3,610,240 A | 10/1971 | Harautuneian | | 128/214.4 |
| 3,658,061 A | 4/1972 | Hall | | 128/214.4 |
| 3,780,734 A | 12/1973 | Wulff | | 128/218 |
| 3,884,230 A | 5/1975 | Wulff | | 128/221 |
| 3,890,971 A | 6/1975 | Lesson et al. | | 128/218 |
| 3,904,033 A | 9/1975 | Haerr | | 206/349 |
| 4,048,997 A | 9/1977 | Raghavachari et al. | | 12/215 |
| 4,170,933 A | 10/1979 | Meamber | | 99/349 |
| 4,170,993 A | 10/1979 | Alvarez | | 128/214 |
| 4,356,822 A | 11/1982 | Winstead-Hall | | 128/215 |
| 4,365,626 A | 12/1982 | House | | 128/218 |
| 4,373,526 A | 2/1983 | Kling | | 128/215 |
| 4,416,663 A | 11/1983 | Hall | | 604/163 |
| 4,425,120 A | 1/1984 | Sampson et al. | | 604/198 |
| 4,573,976 A | 3/1986 | Sampson et al. | | 604/198 |
| 4,631,057 A | 12/1986 | Mitchell | | 604/198 |
| 4,655,751 A | 4/1987 | Harbaugh | | 604/198 |
| 4,664,259 A | 5/1987 | Landis | | 206/365 |
| 4,666,435 A | 5/1987 | Braginetz | | 604/198 |
| 4,681,567 A | 7/1987 | Masters et al. | | 604/198 |
| 4,693,257 A | 9/1987 | Markham | | 128/752 |
| 4,695,274 A | 9/1987 | Fox | | 604/198 |
| 4,702,738 A | 10/1987 | Spencer | | 604/198 |
| 4,702,739 A | 10/1987 | Milorad | | 604/198 |
| 4,737,144 A | 4/1988 | Choksi | | 604/198 |
| 4,743,233 A | 5/1988 | Schneider | | 604/192 |
| 4,772,272 A | 9/1988 | McFarland | | 604/198 |
| 4,795,432 A | 1/1989 | Karczmer | | 604/110 |
| 4,813,940 A | 3/1989 | Parry | | 604/198 |
| 4,816,024 A | 3/1989 | Sitar et al. | | 604/192 |
| 4,826,490 A | 5/1989 | Byrne et al. | | 604/198 |
| 4,846,796 A | 7/1989 | Carrell et al. | | 604/110 |
| 4,846,805 A | 7/1989 | Sitar | | 604/165 |
| 4,850,968 A | 7/1989 | Romano | | 604/110 |
| 4,850,977 A | 7/1989 | Bayless | | 604/198 |
| 4,850,994 A | 7/1989 | Zerbst et al. | | 604/198 |
| 4,863,434 A | 9/1989 | Bayless | | 604/198 |
| 4,863,435 A | 9/1989 | Sturman et al. | | 604/198 |
| 4,867,746 A | 9/1989 | Dufresne | | 604/192 |
| 4,874,384 A | 10/1989 | Nunez | | 604/198 |
| 4,892,523 A | 1/1990 | Haber | | 604/198 |
| 4,894,055 A | 1/1990 | Sudnak | | 604/198 |
| 4,897,083 A | 1/1990 | Martell | | 604/192 |
| 4,900,311 A | 2/1990 | Stern et al. | | 604/198 |
| 4,911,693 A | 3/1990 | Paris | | 604/192 |
| 4,923,445 A | 5/1990 | Ryan | | 604/198 |
| 4,923,447 A | 5/1990 | Morgan | | 604/198 |
| 4,927,018 A | 5/1990 | Yang et al. | | 604/198 |
| 4,927,416 A | 5/1990 | Tomkiel | | 604/198 |
| 4,929,237 A | 5/1990 | Medway | | 604/198 |
| 4,931,048 A | 6/1990 | Lopez | | 604/110 |
| 4,932,940 A | 6/1990 | Walker et al. | | 604/110 |
| 4,932,947 A | 6/1990 | Cardwell | | 604/198 |
| 4,936,830 A | 6/1990 | Verlier | | 604/110 |
| 4,946,446 A | 8/1990 | Vadher | | 604/198 |
| 4,966,592 A | 10/1990 | Burns et al. | | 604/198 |
| 4,969,877 A | 11/1990 | Kornberg | | 604/195 |
| 4,985,021 A | 1/1991 | Straw et al. | | 604/198 |
| 4,998,924 A | 3/1991 | Ranford | | 604/198 |
| 5,000,744 A | 3/1991 | Hoffman et al. | | 604/232 |
| 5,002,537 A | 3/1991 | Hoffman et al. | | 604/232 |
| 5,011,479 A | 4/1991 | Le et al. | | 604/198 |
| 5,013,301 A | 5/1991 | Marotta, Jr. et al. | | 604/197 |
| 5,019,051 A | 5/1991 | Hake | | 604/198 |
| 5,045,066 A | 9/1991 | Scheuble et al. | | 604/198 |
| 5,057,086 A | 10/1991 | Dillard, III et al. | | 604/195 |
| 5,057,087 A | 10/1991 | Harmon | | 604/198 |
| 5,059,185 A | 10/1991 | Ryan | | 604/198 |
| 5,061,251 A | 10/1991 | Juhasz | | 604/198 |
| 5,066,277 A | 11/1991 | Carrell et al. | | 604/110 |
| 5,067,945 A | 11/1991 | Ryan et al. | | 604/198 |
| 5,084,030 A | 1/1992 | Byrne et al. | | 604/198 |
| 5,098,382 A | 3/1992 | Haber et al. | | 604/110 |
| 5,098,403 A | 3/1992 | Sampson | | 604/198 |
| 5,106,379 A | 4/1992 | Leap | | 604/198 |
| 5,116,326 A | 5/1992 | Schmidt | | 604/198 |
| 5,127,910 A | 7/1992 | Talonn et al. | | 604/198 |
| 5,137,521 A | 8/1992 | Wilkins | | 604/198 |
| 5,141,500 A | 8/1992 | Hake | | 604/198 |
| 5,147,303 A | 9/1992 | Martin | | 604/110 |
| 5,147,326 A | 9/1992 | Talonn | | 604/198 |
| 5,152,751 A | 10/1992 | Kozlowski | | 604/192 |
| 5,154,698 A | 10/1992 | Compagnucci et al. | | 604/110 |
| 5,163,918 A | 11/1992 | Righi et al. | | 604/198 |
| 5,169,392 A | 12/1992 | Ranford et al. | | 604/198 |
| 5,176,643 A | 1/1993 | Kramer et al. | | 604/135 |
| 5,176,656 A | 1/1993 | Bayless | | 604/198 |
| 5,176,657 A | 1/1993 | Shields | | 604/232 |
| 5,197,953 A | 3/1993 | Colonna | | 604/110 |
| 5,201,708 A | 4/1993 | Martin | | 604/110 |
| 5,201,720 A | 4/1993 | Boergia et al. | | |
| 5,207,646 A | 5/1993 | Brunel | | 604/110 |
| 5,215,535 A | 6/1993 | Gettig et al. | | 604/198 |
| 5,217,437 A | 6/1993 | Talonn et al. | | 604/198 |
| 5,242,416 A | 9/1993 | Hutson | | 604/192 |
| 5,256,153 A | 10/1993 | Hake | | 604/198 |
| 5,259,841 A | 11/1993 | Hohendorf et al. | | 604/110 |
| 5,267,976 A | 12/1993 | Guerineau et al. | | 604/198 |
| 5,269,766 A | 12/1993 | Haber et al. | | 604/198 |
| 5,271,744 A | 12/1993 | Kramer et al. | | 604/51 |
| 5,279,579 A | 1/1994 | D'Amico | | 604/192 |
| 5,279,584 A | 1/1994 | Dillard, III et al. | | 604/198 |
| 5,300,039 A | 4/1994 | Poulsen | | 604/198 |
| 5,304,149 A | 4/1994 | Morigi | | 604/192 |
| 5,306,258 A | 4/1994 | de la Fuente | | 604/198 |
| 5,308,332 A | 5/1994 | Dillard, III et al. | | 604/110 |
| 5,314,414 A | 5/1994 | Hake et al. | | 604/198 |
| 5,336,185 A | 8/1994 | Lynch et al. | | 604/110 |
| 5,338,303 A | 8/1994 | King et al. | | 604/110 |
| 5,338,310 A | 8/1994 | Lewandowski | | 604/192 |
| 5,342,309 A | 8/1994 | Hausser | | 604/110 |
| 5,342,320 A | 8/1994 | Cameron | | 604/192 |
| 5,344,404 A | 9/1994 | Benson | | 604/110 |
| 5,344,407 A | 9/1994 | Ryan | | 604/192 |
| 5,366,447 A | 11/1994 | Gurley | | 604/192 |
| 5,376,080 A | 12/1994 | Petrussa | | 604/198 |
| 5,382,241 A | 1/1995 | Choudhury et al. | | 604/192 |
| 5,385,555 A | 1/1995 | Hausser | | 604/192 |
| 5,385,557 A | 1/1995 | Thompson | | 604/198 |
| 5,403,288 A | 4/1995 | Stanners | | 604/232 |
| 5,417,660 A | 5/1995 | Martin | | 604/110 |
| 5,429,612 A | 7/1995 | Berthier | | |
| 5,433,712 A | 7/1995 | Stiles et al. | | 604/197 |
| 5,437,647 A | 8/1995 | Firth et al. | | 604/110 |
| 5,445,620 A | 8/1995 | Haber et al. | | 604/232 |
| 5,492,536 A | 2/1996 | Mascia | | 604/197 |
| 5,496,286 A | 3/1996 | Stiehl et al. | | 604/232 |
| 5,498,244 A | 3/1996 | Eck | | 604/198 |
| 5,514,107 A | 5/1996 | Haber et al. | | 604/197 |
| 5,522,812 A | 6/1996 | Talonn et al. | | 604/198 |
| 5,527,294 A | 6/1996 | Weatherford et al. | | 604/198 |
| 5,531,706 A | 7/1996 | De la Fuente | | 604/198 |
| 5,536,257 A | 7/1996 | Byrne et al. | | 604/198 |
| 5,549,572 A | 8/1996 | Byrne et al. | | 604/198 |
| 5,554,122 A | 9/1996 | Emanuel | | 604/110 |
| 5,558,649 A | 9/1996 | Shields | | 604/192 |

| | | | | | | |
|---|---|---|---|---|---|---|
| 5,562,624 A | 10/1996 | Righi et al. ............... 604/110 | | 6,102,893 A | 8/2000 | Aneas ................. 604/110 |
| 5,562,626 A | 10/1996 | Sanpietro ................ 604/110 | | 6,102,894 A | 8/2000 | Dysarz ................ 604/110 |
| 5,569,211 A | 10/1996 | Lekhgolts et al. ........ 604/195 | | 6,106,500 A | 8/2000 | Mahurkar ............ 604/195 |
| 5,573,513 A | 11/1996 | Wozencroft ............ 604/198 | | 6,110,147 A | 8/2000 | Perouse ............... 604/198 |
| 5,573,514 A | 11/1996 | Stiehl et al. ............ 604/198 | | RE36,885 E | 9/2000 | Blecher et al. ........ 604/198 |
| 5,595,566 A | 1/1997 | Vallelunga et al. ....... 604/197 | | 6,117,112 A | 9/2000 | Mahurkar ............ 604/194 |
| 5,601,535 A | 2/1997 | Byrne et al. ............ 604/198 | | 6,123,688 A | 9/2000 | Botich et al. .......... 604/220 |
| 5,609,577 A | 3/1997 | Haber et al. ............ 604/110 | | 6,126,637 A | 10/2000 | Kriesel et al. ......... 604/132 |
| 5,624,400 A | 4/1997 | Firth et al. ............. 604/110 | | 6,129,710 A | 10/2000 | Padgett et al. ........ 604/195 |
| 5,647,849 A | 7/1997 | Kalin .................... 604/111 | | 6,149,630 A | 11/2000 | Robinson ............. 604/198 |
| 5,658,254 A | 8/1997 | Reichenbach et al. ... 604/192 | | 6,156,011 A | 12/2000 | Ruminson ............ 604/192 |
| 5,658,259 A | 8/1997 | Pearson et al. ......... 604/232 | | 6,156,013 A | 12/2000 | Mahurkar ............ 604/195 |
| 5,674,203 A | 10/1997 | Lewandowski ......... 604/197 | | 6,159,184 A | 12/2000 | Perez et al. ........... 604/192 |
| 5,681,291 A | 10/1997 | Galli .................... 604/192 | | 6,162,197 A | 12/2000 | Mohammad ......... 604/195 |
| 5,695,474 A | 12/1997 | Daugherty ............. 604/162 | | 6,171,283 B1 | 1/2001 | Perez et al. ........... 604/192 |
| 5,697,908 A | 12/1997 | Imbert et al. .......... 604/110 | | 6,179,812 B1 | 1/2001 | Botich et al. .......... 604/110 |
| 5,700,246 A | 12/1997 | Stiehl et al. ............ 604/198 | | 6,183,446 B1 | 2/2001 | Jeanbourquin ....... 604/198 |
| 5,713,871 A | 2/1998 | Stock .................... 604/192 | | 6,186,980 B1 | 2/2001 | Brunel ................ 604/110 |
| 5,733,264 A | 3/1998 | Flowers ................ 604/198 | | 6,190,361 B1 | 2/2001 | Gettig et al. .......... 604/192 |
| 5,735,823 A | 4/1998 | Berger .................. 604/192 | | 6,203,527 B1 | 3/2001 | Zadini et al. ......... 604/110 |
| 5,735,827 A | 4/1998 | Adwers et al. ......... 604/263 | | 6,206,853 B1 | 3/2001 | Bonnet ................ 604/110 |
| 5,779,683 A | 7/1998 | Meyer .................. 604/118 | | 6,206,856 B1 | 3/2001 | Mahurkar ............ 604/195 |
| 5,811,061 A | 9/1998 | Martinson et al. | | 6,210,374 B1 | 4/2001 | Malencheck ......... 604/192 |
| 5,817,064 A | 10/1998 | DeMarco et al. ....... 604/198 | | 6,213,977 B1 | 4/2001 | Hjertman et al. ..... 604/117 |
| 5,843,041 A | 12/1998 | Hake et al. ............ 604/198 | | 6,213,987 B1 | 4/2001 | Hirsch et al. ......... 604/263 |
| 5,855,839 A * | 1/1999 | Brunel .................. 264/524 | | 6,217,559 B1 | 4/2001 | Foster ................. 604/195 |
| 5,873,856 A | 2/1999 | Hjertman et al. ....... 604/117 | | 6,224,575 B1 | 5/2001 | Garvin ................ 604/195 |
| 2,876,770 A | 3/1999 | White ................... 128/215 | | RE37,252 E | 7/2001 | Hollister .............. 206/364 |
| 5,879,337 A | 3/1999 | Kuracina et al. ....... 604/192 | | 6,254,575 B1 | 7/2001 | Thorne, Jr. et al. .... 604/198 |
| 5,891,092 A | 4/1999 | Castellano ............. 604/110 | | 6,258,068 B1 | 7/2001 | Kirchhofer et al. ... 604/208 |
| 5,891,105 A | 4/1999 | Mahurkar .............. 604/195 | | 6,261,264 B1 | 7/2001 | Tamaro ................ 604/198 |
| 5,893,845 A | 4/1999 | Newby et al. .......... 604/198 | | 6,261,265 B1 | 7/2001 | Mosseri ............... 604/198 |
| 5,938,641 A | 8/1999 | Villanueva ............ 604/110 | | 6,273,870 B1 | 8/2001 | Garvin ................ 604/110 |
| 5,938,644 A | 8/1999 | Kirk .................... 604/263 | | RE37,439 E | 11/2001 | Firth et al. ............ 604/110 |
| 5,947,933 A | 9/1999 | Reichenbach et al. ... 604/198 | | 6,344,032 B1 | 2/2002 | Perez et al. ........... 604/198 |
| 5,964,739 A | 10/1999 | Champ ................. 604/263 | | 2002/0161337 A1 | 10/2002 | Shaw ................... 604/181 |
| 5,968,019 A | 10/1999 | Lee ..................... 604/195 | | | | |
| RE36,398 E | 11/1999 | Byrne et al. ........... 604/198 | | | | |
| 5,984,899 A | 11/1999 | D'Alessio et al. ...... 604/198 | | | | |
| 5,993,418 A | 11/1999 | Alexander ............. 604/198 | | | | |
| D418,222 S | 12/1999 | Pellow ................. D24/130 | | | | |
| 5,997,513 A | 12/1999 | Smith et al. ........... 604/198 | | | | |
| 6,004,296 A | 12/1999 | Jansen et al. ......... 604/198 | | | | |
| 6,013,059 A | 1/2000 | Jacobs ................. 604/198 | | | | |
| 6,017,329 A | 1/2000 | Hake ................... 604/198 | | | | |
| 6,024,727 A | 2/2000 | Thorne et al. ......... 604/195 | | | | |
| 6,030,366 A | 2/2000 | Mitchell .............. 604/192 | | | | |
| 6,074,370 A | 6/2000 | Pressly, Sr. et al. .... 604/195 | | | | |
| 6,077,253 A | 6/2000 | Cosme ................ 604/263 | | | | |
| 6,080,135 A | 6/2000 | Van Stokkum ........ 604/198 | | | | |
| 6,080,137 A | 6/2000 | Pike .................... 604/263 | | | | |
| 6,090,065 A | 7/2000 | Giles .................. 604/74 | | | | |
| 6,090,077 A | 7/2000 | Shaw .................. 604/195 | | | | |

FOREIGN PATENT DOCUMENTS

| | | |
|---|---|---|
| GB | 0 259 268 | 4/1981 |
| GB | 2 114 006 | 8/1983 |
| GB | 2 202 747 A | 10/1988 |
| GB | 2 202 747 | 10/1988 |
| GB | 2 283 425 | 5/1995 |
| JP | 49-004797 | 1/1974 |
| WO | WO 93/00949 | 1/1993 |
| WO | WO95/04565 | 2/1995 |
| WO | WO 98/35714 | 8/1998 |
| WO | WO 99/25402 | 5/1999 |
| WO | WO 00/33900 | 6/2000 |
| WO | WO01/60435 | 8/2001 |

\* cited by examiner

AUTOMATICALLY OPERABLE SAFETY SHIELD SYSTEM FOR SYRINGES

This application is the National Phase of International Application PCT/GB01/00590 filed Feb. 13, 2001 which designated the U.S. and that International Application was published under PCT Article 21(2) in English.

The present invention concerns automatically operable safety shield systems for use with a syringe, as well as automatically operable safety shield systems comprising a syringe, protecting against needle stick injuries.

Needle stick injuries pose a substantial threat to health since they can frequently result in the transmission of disease from one person to another. Once a needle stick injury occurs then it is typically necessary to screen the injured person for a substantial period for e.g. HIV or hepatitis infection, and it may also be necessary to restrict the type of work they do, or the people they work with. The whole experience, even if the injured person has not been infected, is highly traumatic and extremely costly for healthcare providers. Infection is quite unacceptable if the stick injury could have been prevented in the first place. Needle stick injuries are of particular concern to healthcare professionals who are most frequently exposed to possible contamination and are in most frequent contact with infected patients. The recognition of the dangers posed by needle stick injuries has resulted in a general desire to prevent their occurrence, and various types of safety system are available which either retract the needle or shield it after use in order to minimise the possibility of needle stick injuries. The use of such safety systems is being encouraged and enforced by various pieces of "sharps" legislation in the USA, as well as by healthcare insurers and providers.

Examples of prior art safety systems include EP 0966983, the contents of which are incorporated herein by reference in their entirety. EP 0966983 discloses a shield system for prefilled syringes, comprising an outer syringe holder and an inner shield. In use, a prefilled syringe comprising a barrel having a proximal flange, a distal needle, and containing a plunger, is inserted within the enclosure defined by the outer holder and inner shield and is held by the outer enclosure. When sufficient pressure is exerted on the holder by the syringe barrel (for example by pressure exerted on the plunger when the contents of the syringe barrel have been completely injected) the shield is released and is urged in a distal direction by a spring located between the barrel and shield, putting the shield in an extended position and covering the needle.

However, the prior art devices, including EP 0966983, have a number of disadvantages and potential problems in their design and construction. For example, the devices of EP 0966983 are prone to accidental triggering of the shield mechanism since sufficient force (e.g. caused by accidental dropping) exerted on the syringe barrel will in turn exert sufficient force on the outer holder to trigger the shield mechanism. Also, it would appear that the insertion of a syringe into the outer holder/inner shield arrangement with sufficient force to cause it to be retained by the holder may cause triggering of the shield mechanism. Alternatively, this possibility may be avoided by placing the syringe in the enclosure defined by the holder before engaging the shield with the holder. However, such a method of manufacture of the device is somewhat complicated and cumbersome, and would prevent the sale and distribution of the holder/shield arrangement independent of any syringe to be used with it. In addition, the actual triggering of the shield mechanism requires the discrete step of exerting a greater force on the plunger rod than that applied during injection, and is done subsequent to removal of the needle from the patient (numbered paragraph 27). This means that a potentially unacceptable period exists during which needle sticks may occur, and requires an additional step in the use of the syringe. Another disadvantage encountered is that the spring extends to cover the syringe barrel. This can be particularly problematic when injecting a patient since the contents of the syringe barrel are no longer fully visible when the spring is extended, despite the fact that it may be necessary to see them in order to ensure that a proper dosage of medicament has been administered to a patient. Similarly the extended spring makes it difficult to view any label on the syringe barrel, which may be necessary to confirm that the correct medicament was administered to a patient.

The fact that the shield mechanism, including the shield, spring, trigger mechanism and holder must all be grouped together (see for example FIG. 5 of EP 0966983) means that the safety shield arrangement can be undesirably large.

It is frequently necessary when using syringes to insert the needle at a specific acute angle (for example it may be that a long solid medicament formulation must be inserted subcutaneously within a narrow depth range) in order that "coring" is avoided whereby a core of tissue is cut by the needle, in turn causing tissue bruising and trauma and possibly affecting the efficacy of the injected medicament. Bulky safety shields cannot have a finger grip (flange), or at least one of useful dimensions, around the whole of their perimeter whilst still allowing for a sufficiently acute (i.e. shallow) angle to be achieved between the needle and the patient's skin, and so instead are typically provided with laterally-extending flanges radially opposite one another. They are typically manipulated such that when the needle enters the skin the flanges are positioned such that they do not contact the skin (i.e. they are parallel to the plane of the surface of the skin). However, depressing the plunger (which may require a relatively large amount of force to be exerted in a careful and controlled manner when injecting e.g. a solid medicament formulation) can then prove to be difficult since the flanges are in an inconvenient position. Users sometimes overcome this and gain a good grip on the flanges by rotating the syringe by 90 degrees after the needle has entered the skin (i.e. so that the flanges are perpendicular to the plane of the surface of the skin). However, the large bore and sharp edges of the needle tip may cause the rotation to cut a "core" of tissue from the patient, in the same fashion as a groundsman cuts a hole on a green on a golf course. This is, naturally, problematic and it is desirable to avoid it.

U.S. Pat. No. 5,163,918 discloses a disposable safety syringe having an extendable safety shield. However, its construction is significantly different to that of the present invention and has a number of significant disadvantages which are overcome by the present invention. In particular, these disadvantages result from the syringe barrel forming part of the safety shield mechanism, from the use and location of an exposed spring, from the limited movement which can be achieved with the syringe plunger, and from the safety clips employed with the syringe.

The spring is also exposed when the protective sleeve is not in the retracted position. When moving to the extended position, movement could easily be hindered by the spring catching on e.g. the hand of a user or by snagging on clothing etc. The spring in the device of various embodiments of the present invention is always enclosed and so cannot be interfered with.

The protective sleeve of U.S. Pat. No. 5,163,918 is also provided with finger grips which are held by a user. Their use means that the protective sleeve cannot extend over the needle until after the user has released their grip on either the sleeve or the plunger. Doing this with the needle in the patient could lead to sudden movement of the needle and tissue damage. Therefore the needle can only safely be covered after it has been removed from the patients and is not done so until the user consciously lets go of the protective sleeve or plunger, which can result in the needle being unnecessarily exposed. The present invention provides an automatically operable shield system (i.e. which is operated as a result of the of the plunger rod being filly depressed and without any additional intervention from the user) which covers the needle as it is withdrawn from the patient, ensuring that it is not exposed. The automatically operable system of the present invention allows in a single fluid movement (depression of a plunger rod) both the administration of a medicament to a patient and the operation of the safety shield system.

Specifically, the spring used to extend the protective sleeve over the needle extends over the syringe barrel. As discussed above, this is a disadvantage since it may damage the barrel and can hinder viewing of the contents of the syringe barrel, and therefore it may be difficult or impossible to provide exact metered doses of medicaments. In the case of solid depots to be administered to patients, medical requirements typically require that the presence (or absence) of the depot in the syringe barrel can be easily determined by eye, both before and after injection. The spring occluding the syringe barrel would substantially hinder this.

In order to prevent unwanted triggering of the release mechanism, the plunger of U.S. Pat. No. 5,163,918 is provided with removable safety means comprising either a tearable strip or removable cap through which it is free to move but the release mechanism trigger is not. This can result in an injection being given to a patient, only for the clinician to find that the safety means has not been removed, at which point the plunger must be retracted to allow the removal of the safety means. This may cause discomfort and trauma to the patient. Embodiments of the present invention provide alternate safety means which must be removed prior to movement of the plunger, therefore avoiding the above problem.

Furthermore, the locking mechanism of the present invention makes use (see below) of the outer shield stop member which locked it in place in the retracted position both to prevent its further extension, as well as its retraction. U.S. Pat. No. 5,163,918 instead requires additional tabs to achieve a similar aim, which clearly adds unnecessary complexity to the device. Although not required in the present invention, in certain embodiments additional engagement means are also provided to prevent the unwanted further extension of the outer shield, thus making the present invention more mechanically resilient.

In addition, the design of the syringes of U.S. Pat. No. 5,163,918 inevitably makes them larger (more lengthy) than those of the present invention. When the protective sleeve of U.S. Pat. No. 5,163,918 is moved to its extended position, it is left covering a substantial portion of the syringe barrel. This means that in order to cover a large needle, a lengthy protective sleeve and therefore a lengthy syringe barrel is necessary. This can make the overall syringe somewhat unnecessarily large and unwieldy, and its size can cause concern to patients. In contrast, when in its extended position the outer shield of the present invention is left covering a relatively insubstantial portion of the syringe barrel. This means that the devices of the present invention can be smaller and more convenient.

In manufacturing terms the syringes of U.S. Pat. No. 5,163,918 must be manufactured and sold as complete items. The present invention allows for the manufacture of the syringe, optionally containing a medicament, separately from the manufacture of the safety shield arrangement, the two being subsequently combined. This means that a stock of safety shields can be prepared without needing to incur the costs of manufacturing complete devices. Similarly, a wide range of syringes pre-filled with medicaments can be kept, and combined with safety shields as and when necessary. Overall this can allow for smaller stocks of components to be kept (thereby saving money for the manufacturer) and for the manufacturing process to respond rapidly to demand for any particular product.

The present invention also provides the advantage over U.S. Pat. No. 5,163,918 when a syringe is to be filled by a clinician and then used with it—the prior art device only allows for the partial movement of the plunger, meaning that when filling the syringe it will inevitably end up containing air which must subsequently be removed. This removal of air can be extremely difficult, if not impossible, and injecting air into a patient typically causes tissue damage. The present invention allows full movement of the plunger in the syringe barrel, and so air can be expelled prior to drawing medicament into the syringe. The filled syringe can then be combined with a safety shield arrangement and the medicament administered to the patient.

Other safety shield arrangements include those of U.S. Pat. Nos. 5,201,720, 5,271,744, 5,855,839, 4,850,968 and those referenced by EP 0966983.

Thus, the present invention overcomes the prior art disadvantages and provides an alternative and improved safety shield system for syringes. Particular advantages of the present invention are that it is less bulky than prior art devices, that the safety shield mechanism is substantially less prone to being accidentally triggered and is resilient to attempts to force apart holder and shield for example by exerting force on the syringe barrel, that the safety shield mechanism is activated by the movement of the plunger rod rather than by pressure exerted on the syringe barrel, and can be achieved as an integral part of the injection process rather than as an additional discrete step, and that in various embodiments its spring does not extend substantially over the syringe barrel, According to the present invention there is provided an automatically operable safety shield system for use with a syringe, said safety shield system comprising:

an inner holder having proximal and distal portions and defining an enclosure into which said syringe may be inserted;

an outer shield having proximal and distal portions, mounted outwards from said inner holder and being axially movable relative to said inner holder between retracted and extended positions;

a spring positioned between a first detent on said inner holder and a second detent on said outer shield, and urging said outer shield to its extended position, said spring preferably positioned between a first distal detent on said inner holder and a second distal detent on said outer shield;

said inner holder having at least one first opening and said outer shield having at least one first stop member, said first stop member being engageable with said first opening when said outer shield is in said retracted position;

said inner holder having distal to said first opening at least one first indentation, said first stop member being engageable with said first indentation when said outer shield is in said extended position; and a trigger positioned within said inner holder and axially movable relative to said inner holder such that it can contact said first stop member when it is engaged with said first opening and disengage said first stop member from said first opening, allowing said spring to move said outer shield to said extended position.

Syringes are ordinarily comprised of a generally cylindrical portion, known as a barrel, a needle or other piercing or connecting element secured to one end of the barrel, and a piston or stopper slidably positioned within the barrel. A plunger rod is typically engaged with the piston such that movement of the plunger rod causes movement of the piston. The needle may be removably secured to the barrel, or it may be permanently secured to the barrel. The plunger rod may be slidable from a drawn-back extended (proximal-most) position in which it can contain medicament to a distal most (forwardmost) position in which any medicament is expelled.

The automatically operable safety shield system may additionally comprise a syringe comprising a barrel, a needle, a piston and a plunger rod movable within said barrel, said plunger rod having a protrusion, said syringe being operationally coupled to said trigger such that movement of said plunger rod protrusion to contact said trigger causes disengagement of said first stop member from said first opening, allowing said spring to move said outer shield to said extended position.

The first and second detents may be positioned as desired on the inner holder and outer shield, for example at their distal or proximal ends. However, the positioning of the first and second detents at the distal portions of the inner holder and outer shield is most preferred since this allows the spring to be kept covered by the outer shield at all times, and for the spring not to extend over the syringe barrel even when the outer shield is in its extended position.

Springs used in the systems of the present invention are typically (but not necessarily) coil springs, and a person skilled in the art will be aware of alternative springs which may be used in the invention. The skilled person will also be aware of variants of coiled springs, such as tapered coil springs and coil springs with variable coiling along their length, which are equally useful in the present invention.

Also provided according to the present invention is an automatically operable safety shield system, comprising:

a syringe comprising a barrel, a needle, a piston and a plunger rod movable within said barrel, said plunger rod having a protrusion;

an inner holder having proximal and distal portions and defining an enclosure into which said syringe may be inserted;

an outer shield having proximal and distal portions, mounted outwards from said inner holder and being axially movable relative to said inner holder between retracted and extended positions;

a spring positioned between a first distal detent on said inner holder and a second distal detent on said outer shield, and urging said outer shield to said extended position;

said inner holder having at least one first opening and said outer shield having at least one first stop member, said first stop member being engageable with said first opening when said outer shield is in said retracted position;

said inner holder having distal to said first opening at least one first indentation, said first stop member being engageable with said first indentation when said outer shield is in said extended position; and said syringe being operationally coupled to said inner holder and outer shield such that axial movement of said plunger rod protrusion relative to said inner holder causes said plunger rod protrusion to contact said first stop member when it is engaged with said first opening and disengage said first stop member from said first opening, allowing said spring to move said outer shield to said extended position.

In order to prevent unwanted movement of the syringe plunger rod, the syringe may be provided with a safety clip removably secured to the portion of said plunger rod exposed from said barrel such that movement of said plunger rod is prevented when said safety clip is secured to said plunger rod.

Said outer shield and inner holder may have, respectively, proximal and distal abutment surfaces in opposing relationship to one another, which can engage one another to prevent movement of said outer shield beyond its extended position.

The inner holder and outer shield may be of any desired shape. For example, they may be of a generally cylindrical shape. An example of a cylinders is one having a circular cross-section (commonly referred to as a right circular cylinder). Alternatively, a cylinder may have an elliptical cross-section. This may be particularly useful in ensuring that the inner holder and outer shield cannot be put together in an incorrect arrangement, or rotated relative to one another during use. Cylinders include those that are slightly tapered, for example by at least 0.5 degrees.

The inner holder and outer shield may also be constructed so as to avoid their relative rotation by providing guide means for their axial movement. Guide means may take the form of grooves in the inner holder and/or outer shield. For example, the first stop members may slide along a groove on the inner holder. Similarly, the outer shield proximal abutment surface may be guided towards the inner holder distal abutment surface by a groove on the outer shield.

The inner holder an/or outer shield may each be formed as a single piece, or may be constructed from more that one piece. Such construction will be readily apparent to a person skilled in the art.

All embodiment of the present invention provide the distinct advantage over the prior art of it being the movement of the plunger rod, rather than of e.g. the syringe barrel, which enables the spring to move the shield to the extended position. This is typically the position where the plunger rod is fully depressed and the contents of the syringe have been expelled and e.g. injected into a patient. The disengagement of the first stop member from the first opening may be achieved either by direct contact of a plunger rod protrusion with the first stop member, or by an indirect communication of the plunger rod protrusion with the first stop member.

Direct contact may be achieved by e.g. providing the plunger rod with a thumb stop which has an axial extension which, when the plunger rod is depressed, contacts the first stop member. Alternatively, the plunger rod may for example be provided with a thumb stop and an additional protrusion which, when the plunger rod is depressed, contacts the first stop member.

Indirect contact may be achieved by any arrangement which can communicate movement caused by the plunger rod (or plunger rod protrusion) to the first stop member. The exact nature of the arrangement will depend on the construction of the plunger rod. For example a plunger rod may have a thumb stop which, when the plunger rod is depressed, contacts a member (such as said trigger) located within the inner holder which in turn contacts the first stop member and causes its disengagement from the first opening. The first stop member may be lockably engageable with the first indentation. It may engage the first indentation such that axial movement, both distal and proximal, of the outer shield relative to the inner holder is prevented. The inner holder first indentation may be replaced by any other arrangement or means, for example a protruding member such as an escarpment of frustoconical portion which inhibits the relative movement of the inner holder and outer shield, although the prevention of any axial movement is preferred.

The first distal detent may protrude outwardly from the inner holder, and the second distal detent may protrude inwardly from the outer shield.

The syringe may be retained within the inner holder by any appropriate means. For example, in order to ensure the correct positioning of the syringe relative to the inner holder the syringe may abut an inner holder detent, for example an upper surface of an inner holder first distal flange. It may also be advantageous to provide the inner holder with syringe engagement means for engaging and retaining the syringe. For example, the inner holder and syringe barrel may be designed so that they make an interference fit, the syringe once inserted into the inner holder only being removable with the application of substantial force, for example of at least 50N, more particularly at least 70–80N or 100N.

Thus the syringe may be axially immovable relative to the inner holder.

The use of an interference fit (also referred to as a friction fit) obviates the need for other retaining mechanisms for the syringe, for example frustoconical portions formed in the inner holder to retain the syringe within a certain area. This in turn means that the syringe need not have any flanges as are typically provided in the form of finger grips, allowing for the syringe to be of smaller dimensions than those used in prior art devices and therefore for the safety shield arrangement to be smaller. It may of course be desirable to retain at least a small flange simply to aid in the manipulation of the syringe barrel during the manufacture of the syringe, particularly in the case of prefilled syringes.

The skilled person will be familiar with a number of materials suitable for the construction of the inner holder and the outer shield of the device. Preferably the material is sufficiently clear to allow the contents or label of a syringe inserted into the inner holder to be viewed. Suitable materials include: polystyrene, modified polystyrenes and polystyrene copolymers, polycarbonates, polyether sulphones, polypropylenes, cyclic olefine copolymer resins, copolyesters such as Eastar (RTM) copolyester DN003 [copolyester made from terephthalic acid (or dimethyl terephthalate), ethylene glycol and 1,4 cyclohaxanedimethanol], and acrylonitrile butadiene styrene copolymer (ABS). A particularly preferred material is Eastar (RTM) copolyester DN003 (Eastman Chemical Company). Also useful are MABS (methyl methacrylate acrylonitrile/butadiene/styrene copolymer, grade Terlux2812 TR (RTM)). Polycarbonates include Lexan (RTM) GR 1210 and Lexan 124R-112. Cyclic olefine resin copolymers include Topas (RTM) 6013 X5.

For some applications, devices of the present invention may be required to be supplied in a sterile state. The skilled person will be familiar with the sterilisation of pharmaceutical devices and the methods for the sterilisation of such devices, for example using heat, gaseous techniques or gamma irradiation. The physical properties of materials used in the construction of devices of the present invention for sterilisation is required to be not substantially affected by the sterilisation. For example, in some materials the sterilisation process may introduce stress fractures or change the material from being clear to being opaque. A preferred method for sterilisation of devices of the present invention is gamma-irradiation. However, gamma-irradiation can induce changes in the colour of plastic materials and can also cause stress fractures in plastic materials. We have found that gamma-irradiation of Eastar (RTM) copolyester DN003 produces substantially no colour changes and does not substantially affect the physical properties of the material. Thus, a preferred material for devices of the present invention suitable for sterilisation by gamma-irradiation is Eastar (RTM) copolyester DN003.

The syringe barrel may be constructed from polypropylene. Alternatively, the syringe barrel may be divided into a number of sections. For example it may comprise upper and lower portions made of high density polythene engaging and retaining a transparent section, for example comprising glass or polystyrene. The lower portion may engage the inner holder. The transparent section may be lensed to provide a magnified view of the contents of the syringe barrel.

In the case of syringe barrels having no flanges or reduced size flanges, the inner holder may be arranged such that the inserted syringe barrel acts to minimise the possibility of accidental disengagement of the first stop member and first opening by e.g. fingers or other small objects being inserted into the inner holder, and the syringe plunger rod may have a flange with a protrusion, for example an axially protruding collar which, when the plunger rod is depressed, passes around the outside of the syringe barrel and contacts, either directly or indirectly, the first stop member to cause its disengagement.

The reduced dimensions of the inner holder and outer shield (relative to prior art shield and holder arrangements) allow for the provision of at least one radially extending protrusion usable as a finger grip, for example a flange of usable dimensions, for example extending at least 2 mm, 3 mm, 4 mm or 5 mm, around the whole of the circumference of the proximal end of the inner holder. This still allows even large bore needles to be inserted into a patient at an angle which does not cause coring. This is particularly useful since it enables the user to readily hold the inner holder at a variety of positions and allows hand positions to be changed without losing the grip required for a satisfactory injection, or without necessitating rotation of the syringe and the possible coring which might result.

The outer shield (rather than the inner holder) may be free (i.e. it may not have) at its proximal end of radially extending protrusions, such as tabs or a flange, useable as a finger grip.

The syringes used with the present invention may be used with liquids, suspensions such as microparticle formulations or solid medicament formulations (also referred to as depots) to be injected subcutaneously. Such injections of depots require that the syringe piston extends through the bore of the syringe needle to ensure that the solid medicament formulation has been wholly expelled from the syringe. The protruding piston can act to lessen the chance of needle sticks if the needle is exposed for any reason, and thus retaining the piston in its extended position by for example ensuring that the depressed plunger rod cannot be pulled back can therefore provide a useful additional safety feature. Examples of microparticle formulations which may be used with the invention include the leuprolide microparticle formulation Lupron (RTM). Examples of solid medicaments which may be used with the present invention include the goserelin depot formulation Zoladex (RTM).

The inner body may additionally comprise plunger rod retaining means, which prevents backwards movement of said plunger rod when it is at least almost at its forwardmost position. As mentioned above, the plunger rod is slidable between an extended position and a forwardmost position. At its forwardmost position the plunger rod causes the disengagement of the first stop member from the first indentation, and it is typically this forwardmost position at which it is desirable to retain the plunger rod, although it may also be desirable to retain the plunger rod at a position almost at the forwardmost position. For example the plunger rod retaining means may comprise a deflectable member or members, for example a frustoconical arrangement or an escarpment or so-called slip back prevention teeth, in the inner holder which allows the plunger rod to be depressed past an upper (i.e. proximal) inclined surface (typically, by elastically deforming it) but which provides a lower (i.e. distal) abutment surface which prevents removal of the plunger rod.

This also provides a number of additional advantages to the invention. Firstly, in various embodiments of the invention, particularly those which use e.g. a trigger to communicate movement of the plunger rod to the first stop member, the plunger rod retaining member can make it more difficult to accidentally (or intentionally) force the disengagement of the first stop member from the first indentation by e.g. jamming fingers into the gap formed between the plunger rod and the inner body to move the trigger, simply by reducing the size of the gap. Secondly, if, somehow, after the apparatus of the invention have been used and the outer shield is in the extended position, sufficient mechanical damage is caused to the apparatus that the outer shield is able to move back towards its retracted position, the first stop member will not be able to re-engage the first indentation and therefore the outer shield will always be urged by the spring back towards its extended position.

The arrangement of the spring with the first and second distal detents of the inner holder and outer shield means that when extended the spring covers an area from the inner holder first distal detent to the outer shield second distal detent, i.e. the spring does not expand to cover the syringe barrel. Therefore, when the inner holder is made of a transparent material, it is possible even after extension of the outer shield to view the contents of the inner holder, meaning that in the case of medicament formulations the complete expulsion of the contents of the syringe may be readily confirmed at any time.

The fact that the spring does not extend to cover the syringe barrel also provides the useful advantage that the spring cannot damage the syringe barrel, such damage being a recognised problem in the prior art which frequently necessitates the use of an additional protecting member when e.g. using a syringe having a glass barrel (see for example EP 0966983 column 7 lines 19–21).

In order to ensure that the squeezing of the shield system by a user does not prevent it from working, the inner holder may be provided with a finger grip area comprising a flange and a rigid section of the inner holder. Squeezing of this will not cause the inner dimensions of the inner holder to be reduced and therefore the safety shield system will function correctly.

The first stop member may engage an abutment surface of the first opening. The first stop member may be provided in the form of an arced flexible member extending from the outer shield, i.e. extending outwardly and then inwardly. Such an arrangement may allow for the first stop member when engaged with the abutment surface of the first opening to have the centre of its pivotal axis inwards of the point of engagement. This means that if an attempt is made, either accidentally or intentionally, to disengage the first stop member and first opening by pulling them apart, they will in fact engage one another more strongly than before and thereby resist being pulled apart. This is a feature lacking in other prior art devices which for example have flexible stop members which disengage upon the exertion of sufficient force.

The invention will be further apparent from the following description together with the drawings of the accompanying Figures which show, by way of example only, one form of safety shield and syringe arrangement. Of the Figures.

Figure 1:
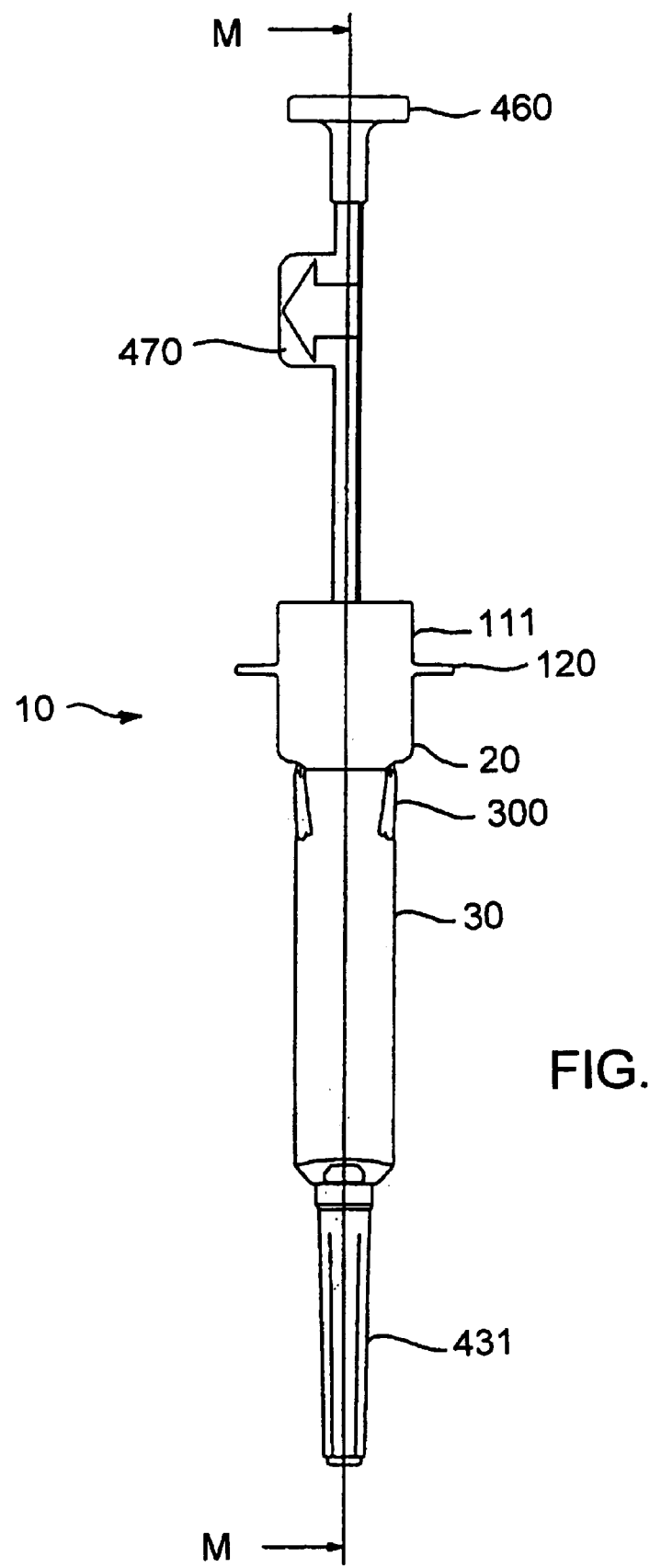
FIG. 1 shows a side view of a safety shield and syringe arrangement of the invention, having an outer shield in its retracted position.
Figure 2:
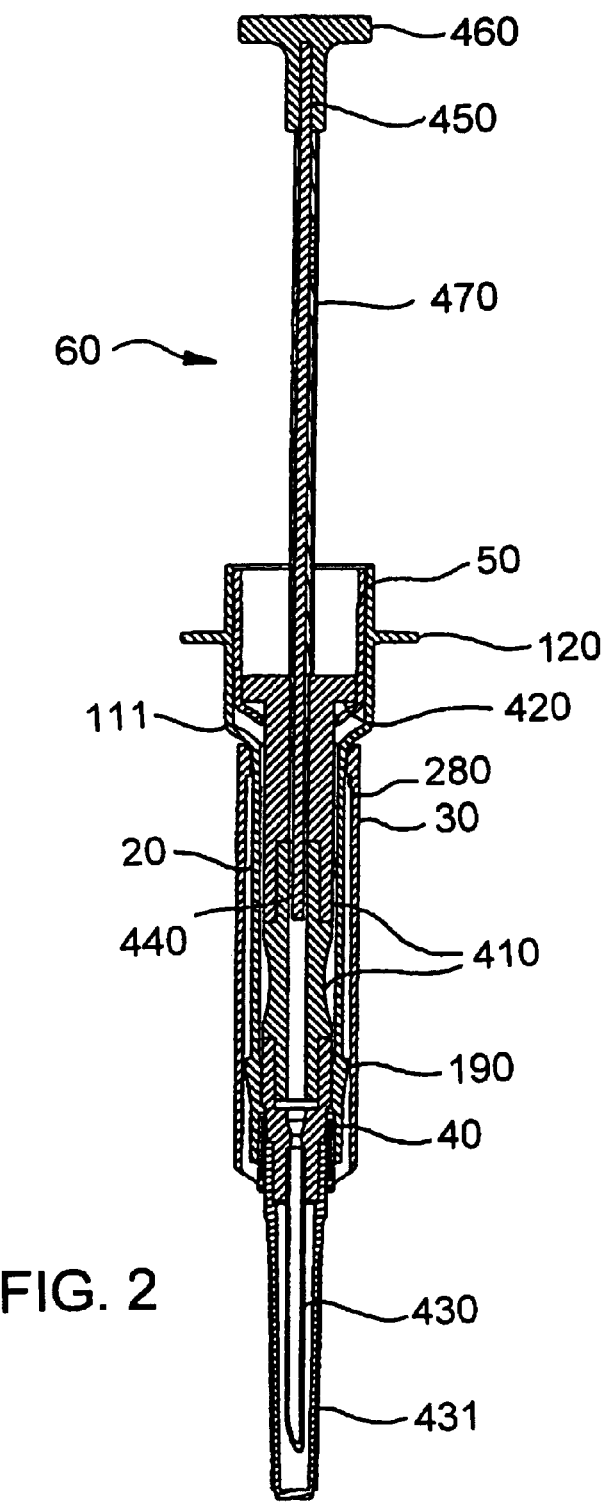
FIG. 2 shows a section on line M—M of FIG. 1.
Figure 3:
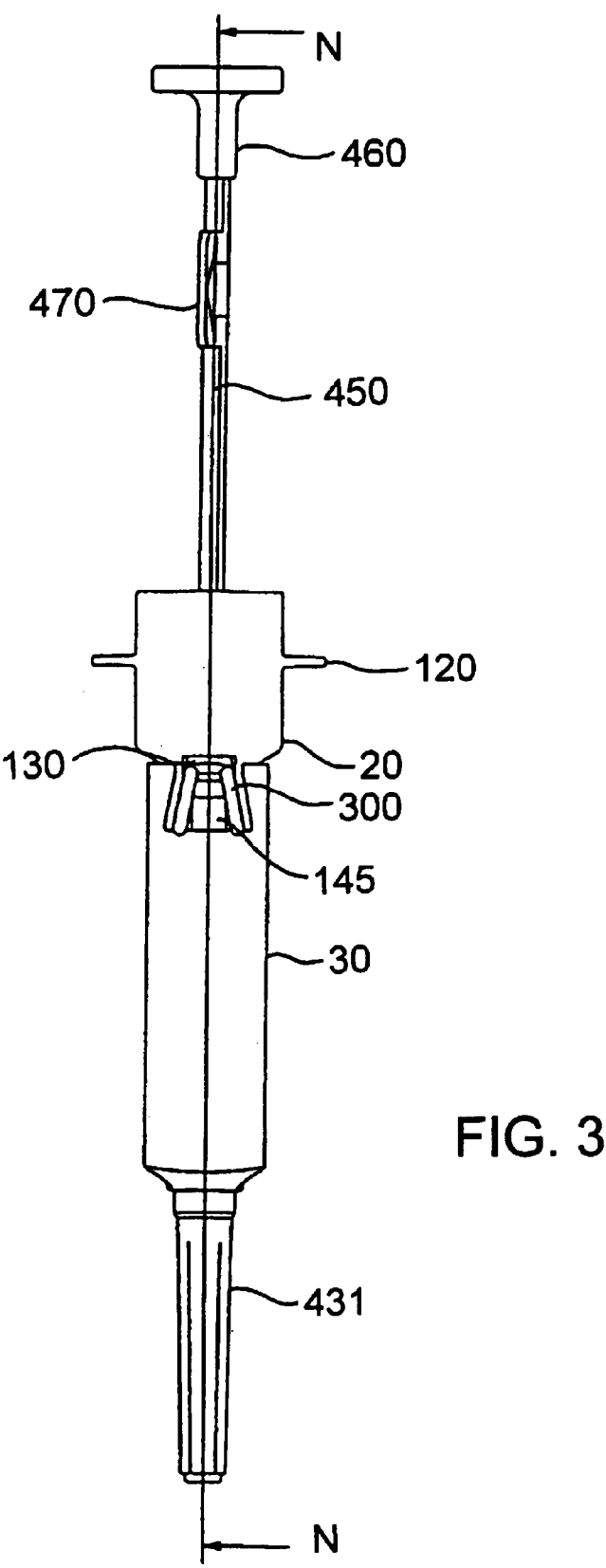
FIG. 3 shows a side view of the arrangement of FIG. 1, having been axially rotated through 90 degrees.
Figure 4:
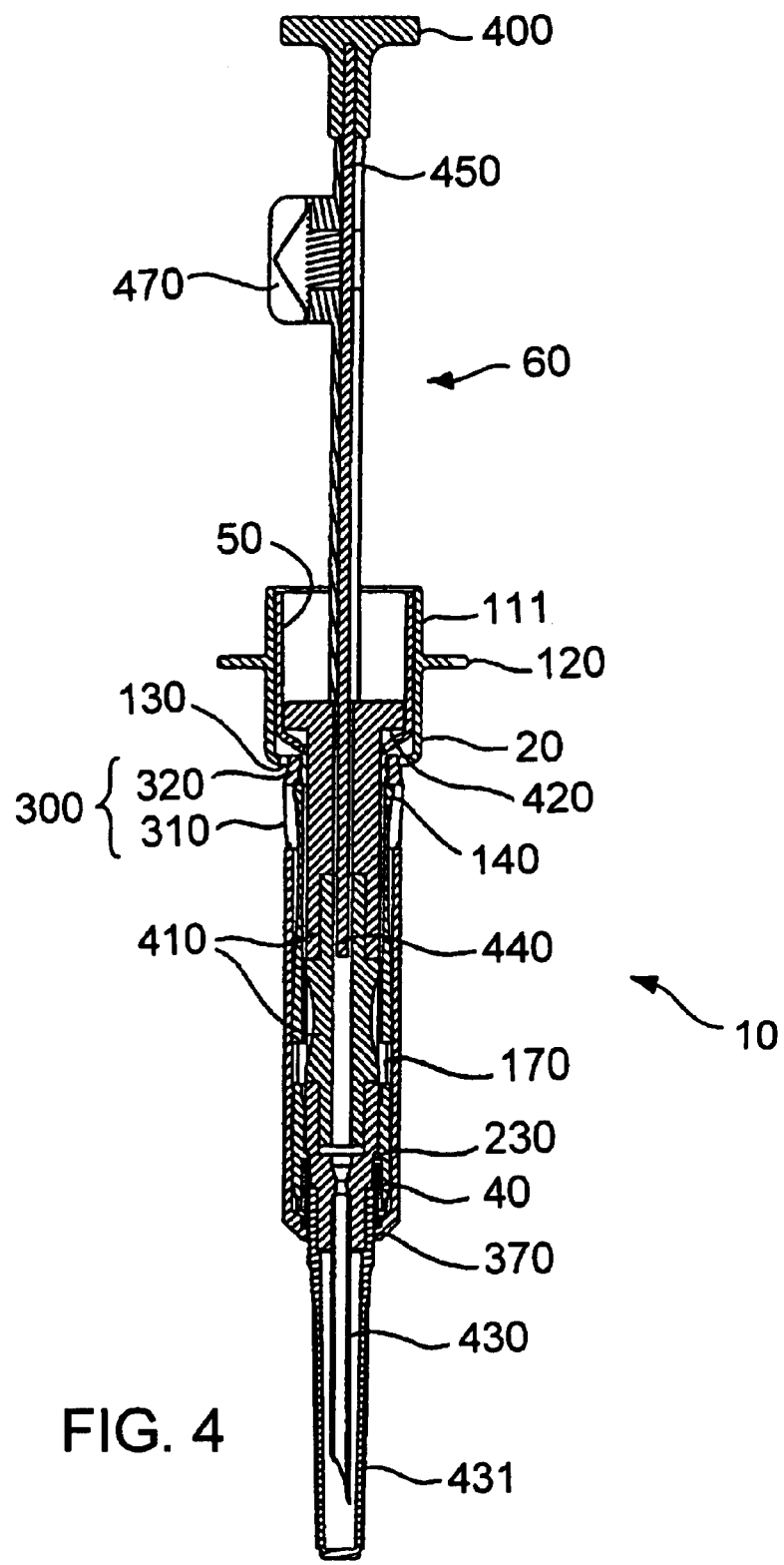
FIG. 4 shows a section on line N—N of FIG. 3.
Figure 5:
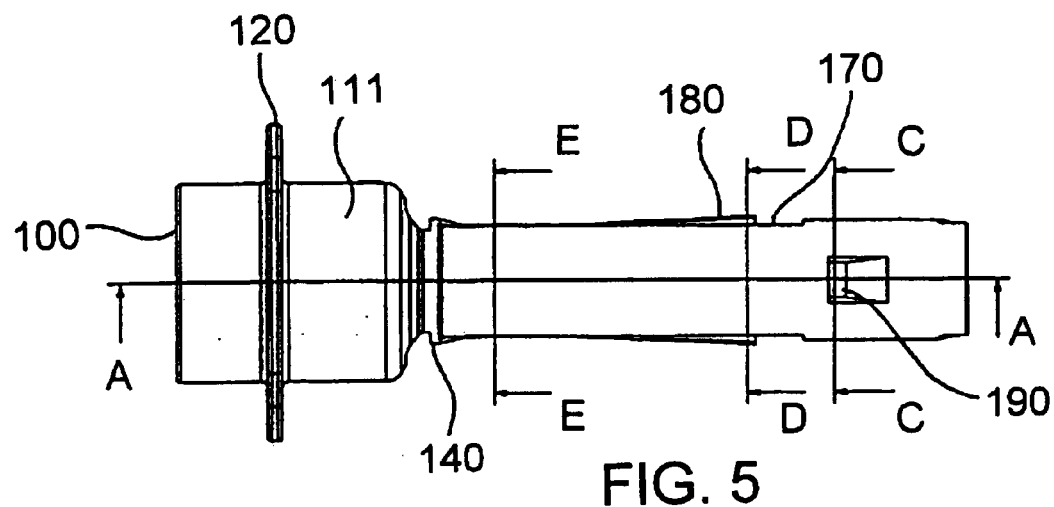
FIG. 5 shows a side view of an inner holder.
Figure 6:
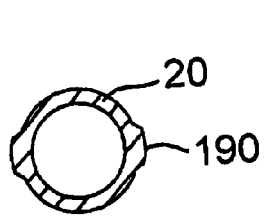
FIG. 6 shows a section on line C—C of FIG. 5.
Figure 7:
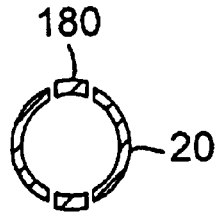
FIG. 7 shows a section on line D—D of FIG. 5.
Figure 8:
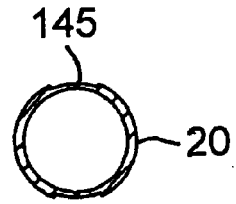
FIG. 8 shows a section on line E—E of FIG. 5.
Figure 9:
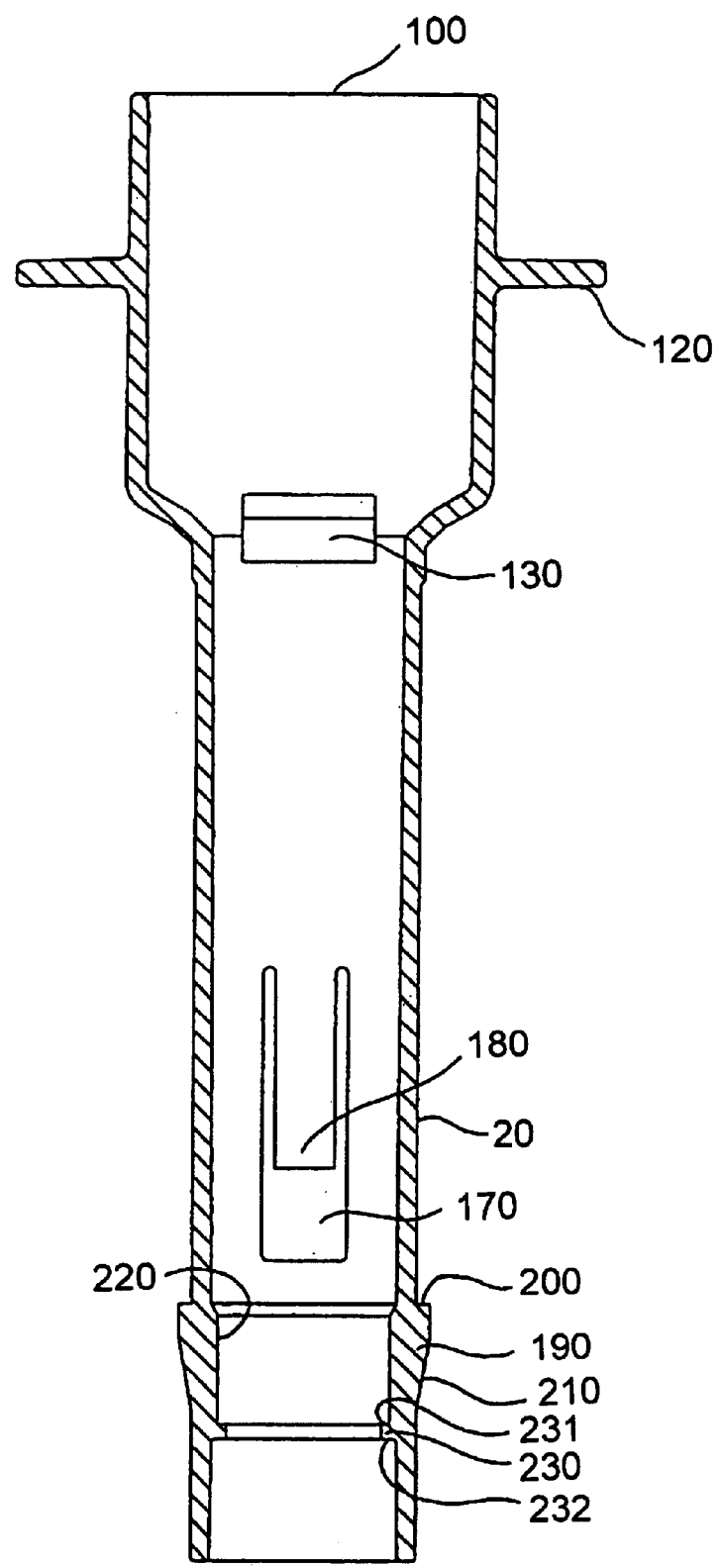
FIG. 9 shows a cut-away view along line A—A of FIG. 5.
Figure 10:
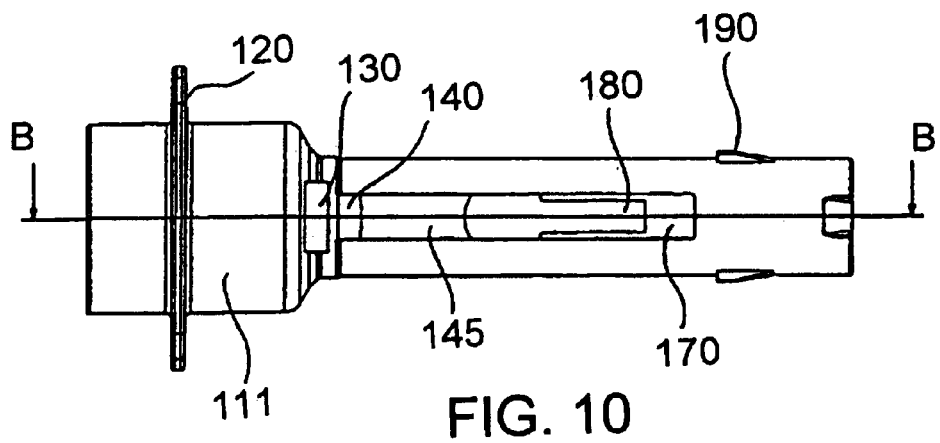
FIG. 10 shows a side view of the inner holder of FIG. 5, having been axially rotated through 90 degrees.
Figure 11:
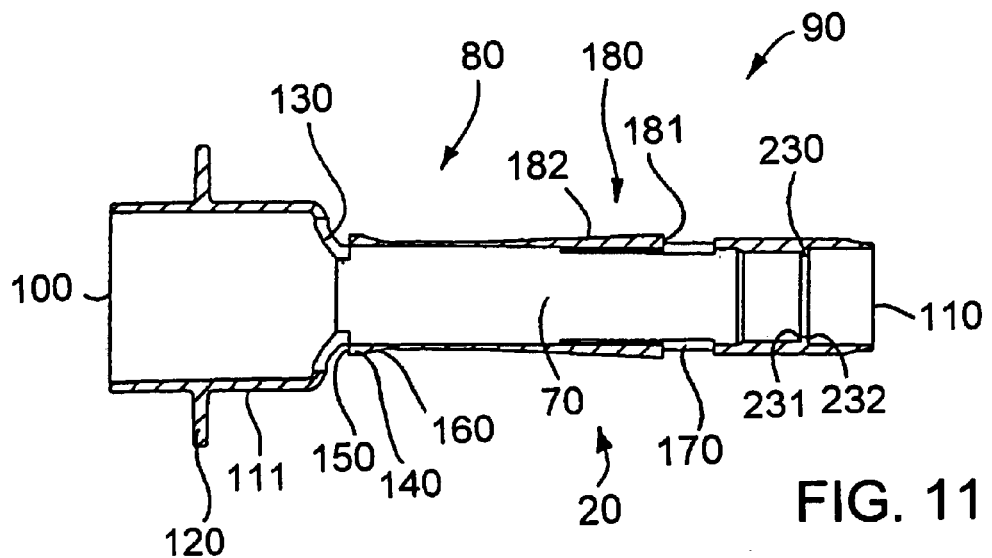
FIG. 11 shows a section on line B—B of FIG. 10.
Figure 12:
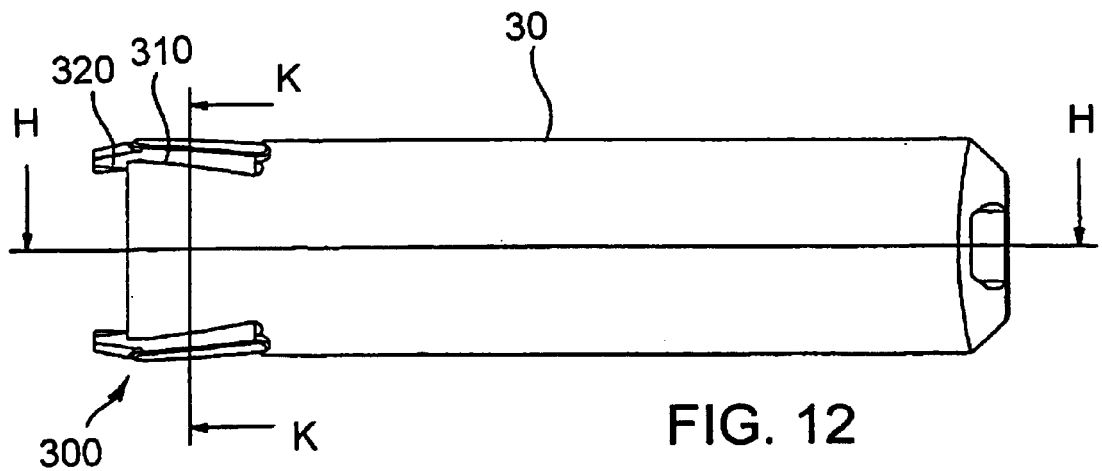
FIG. 12 shows a side view of an outer shield.
Figure 13:
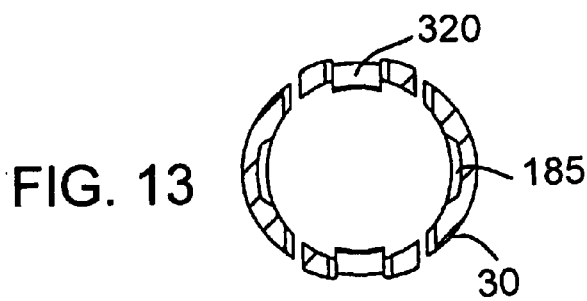
FIG. 13 shows a section on line K—K of FIG. 12.
Figure 14:
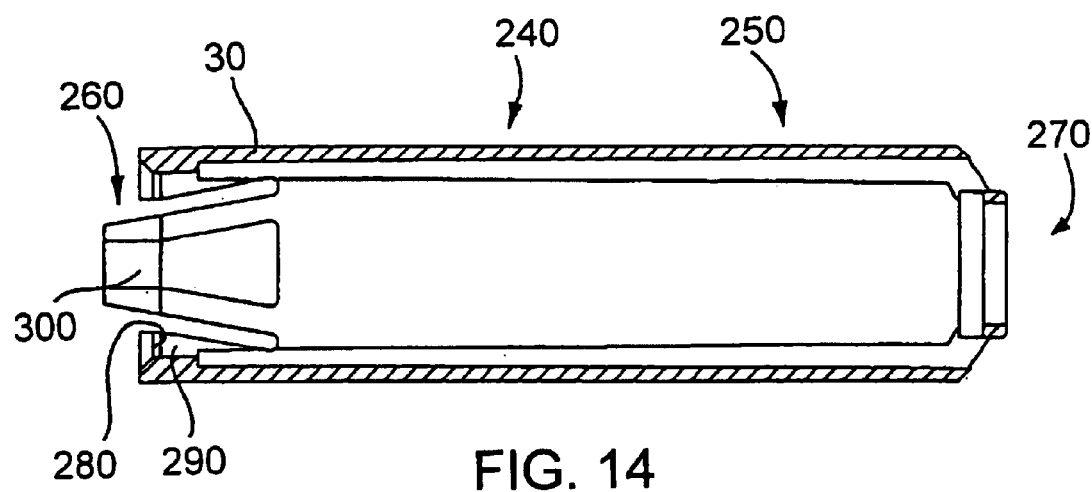
FIG. 14 shows a cut-away view along line H—H of FIG. 12.
Figure 15A:
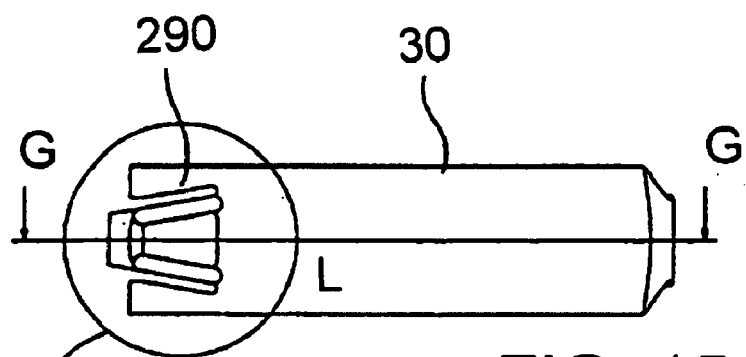
FIG. 15 shows a side view of the outer shield of FIG. 5, having been axially rotated through 90 degrees.
Figure 15B:
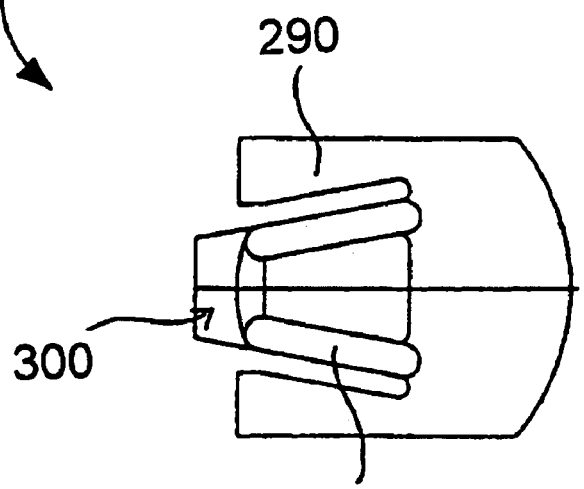
Figure 16:
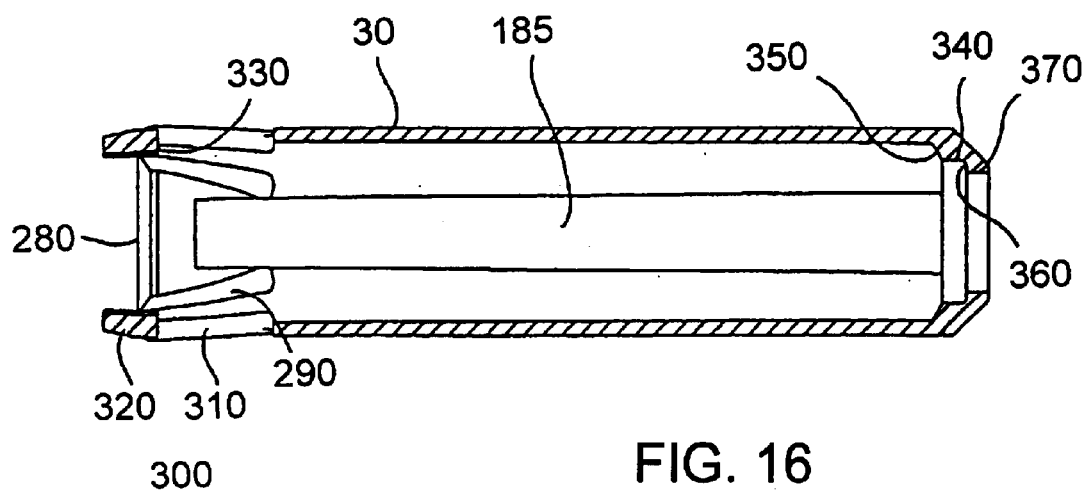
Figure 17:
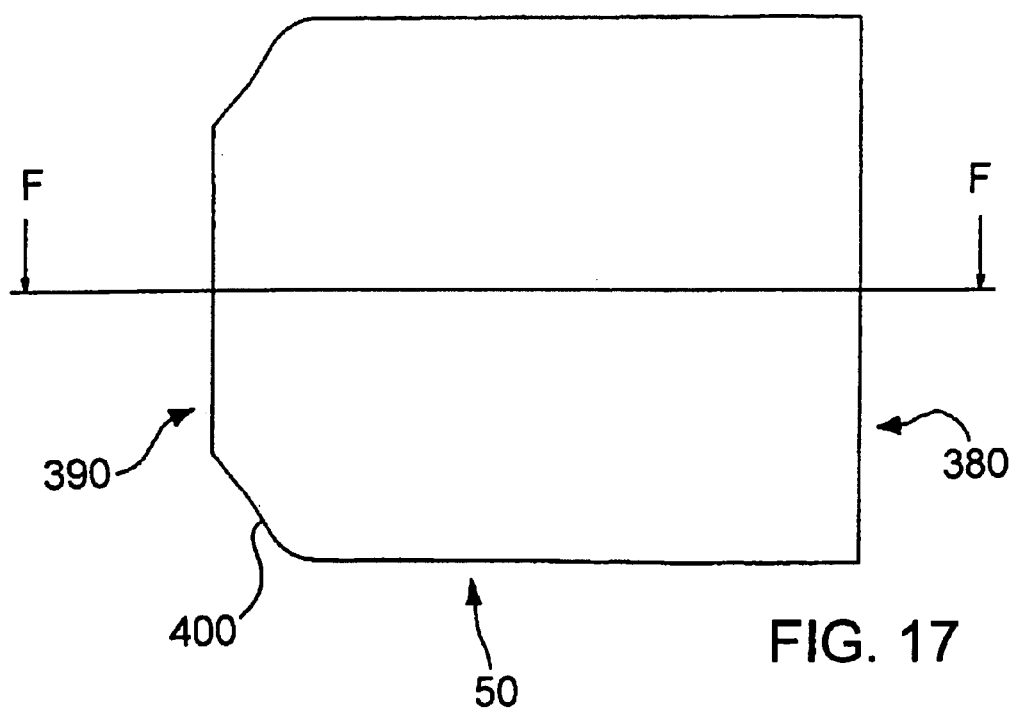
Figure 18:
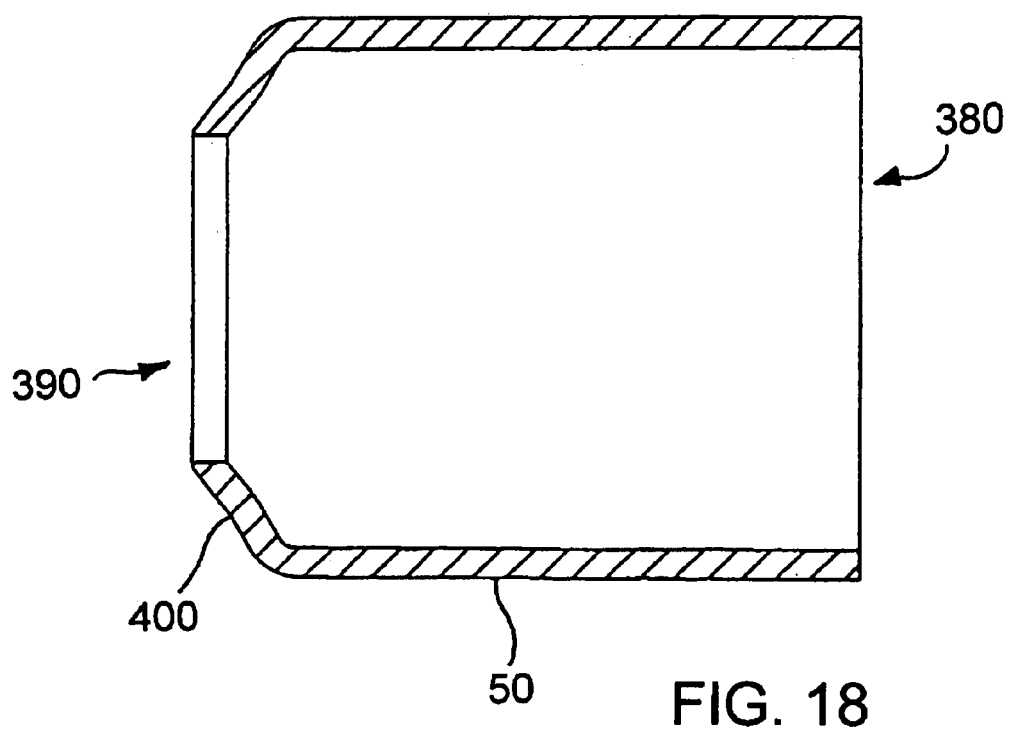
Figure 19:
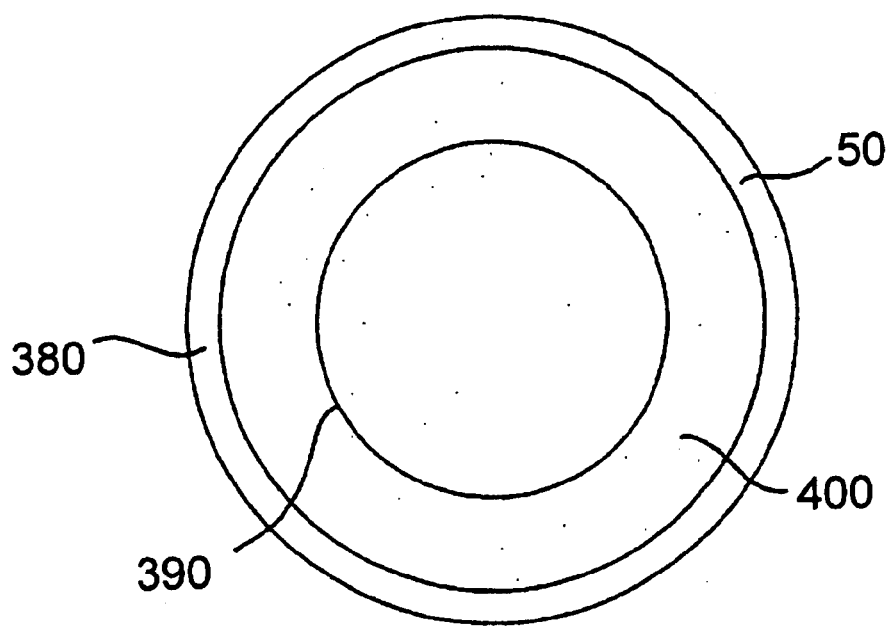
Figure 20:
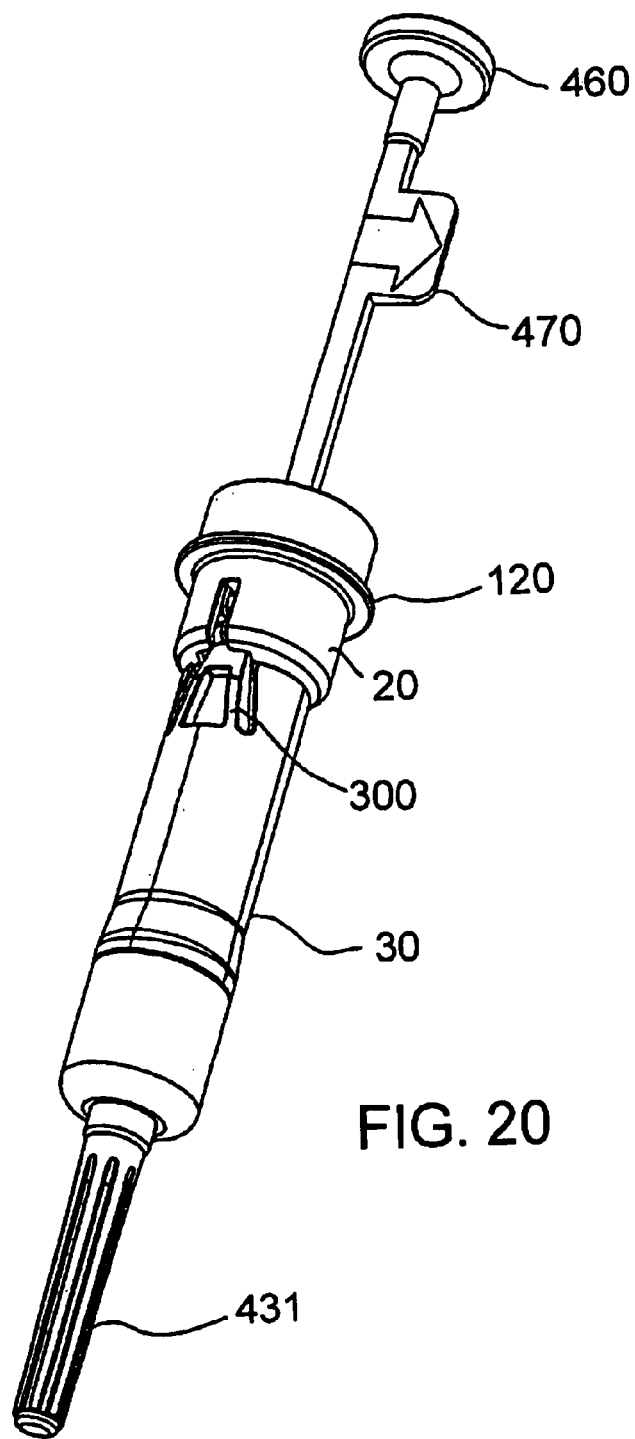
Figure 21:
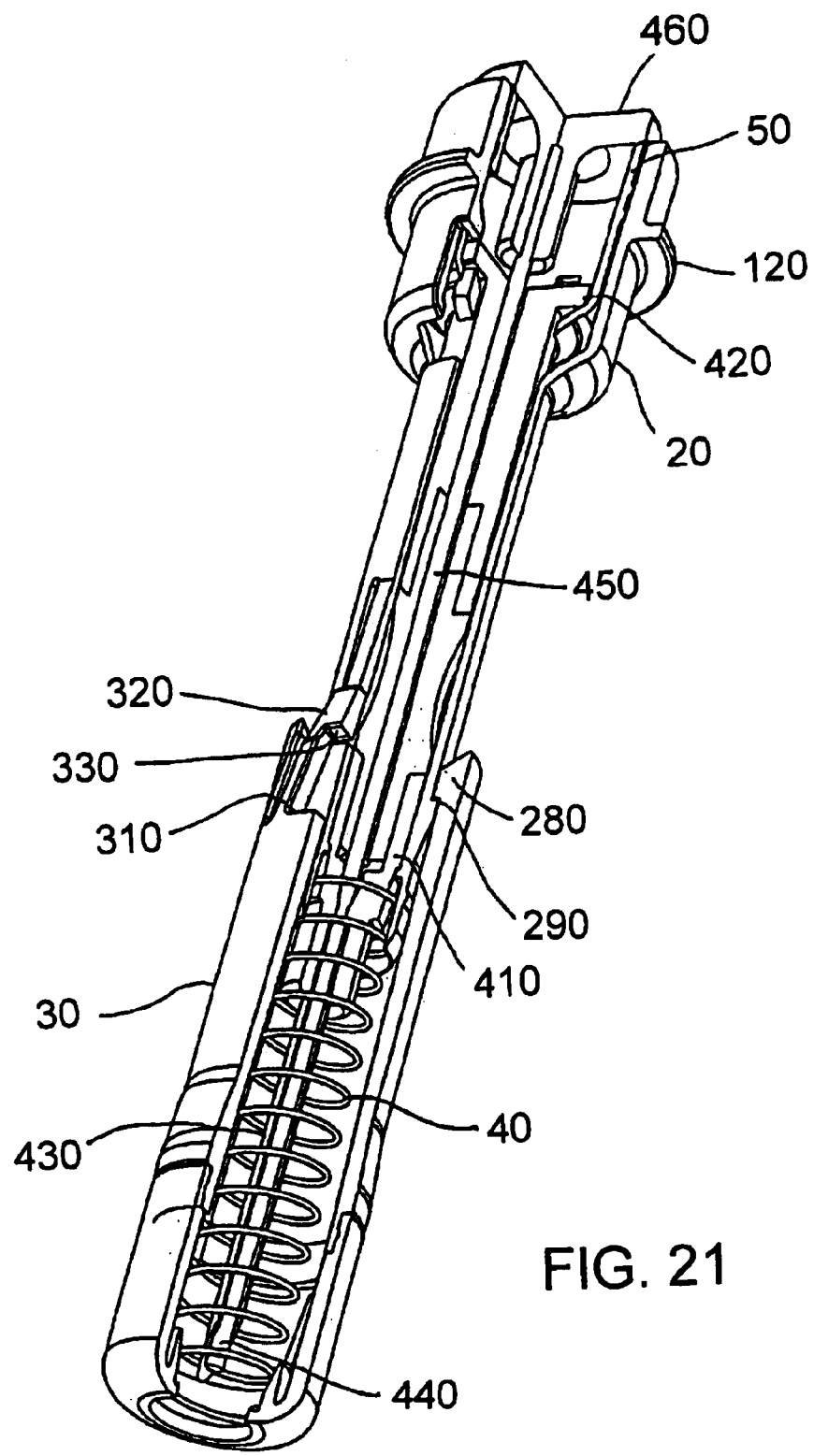
Figure 22:
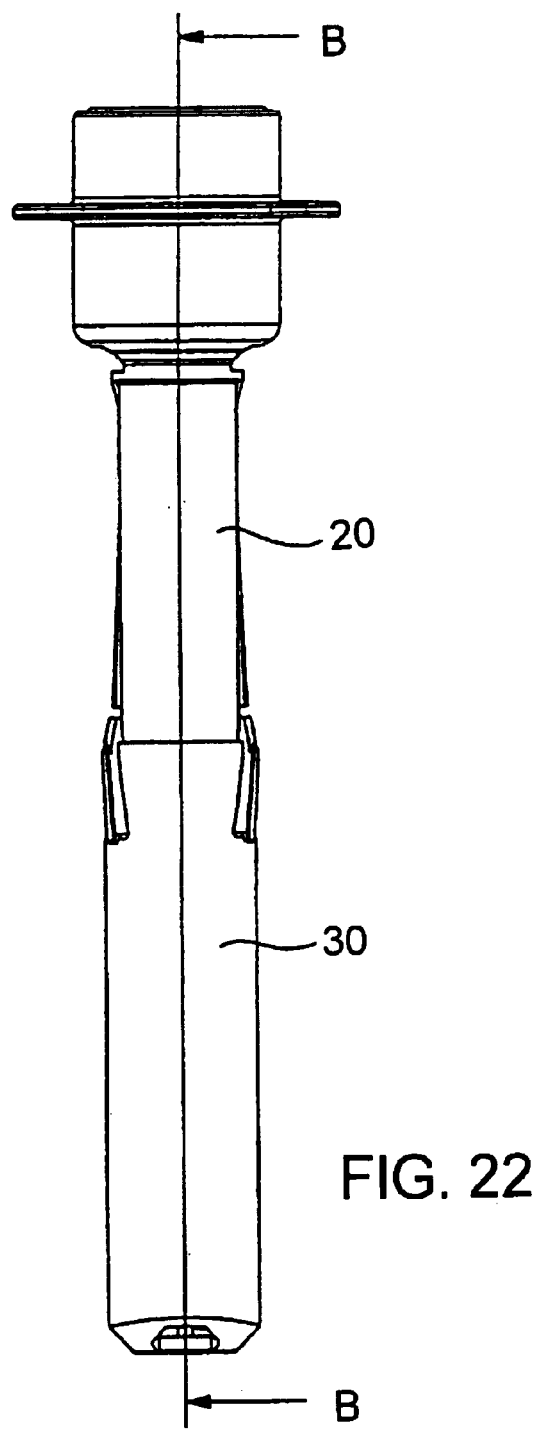
Figure 23:
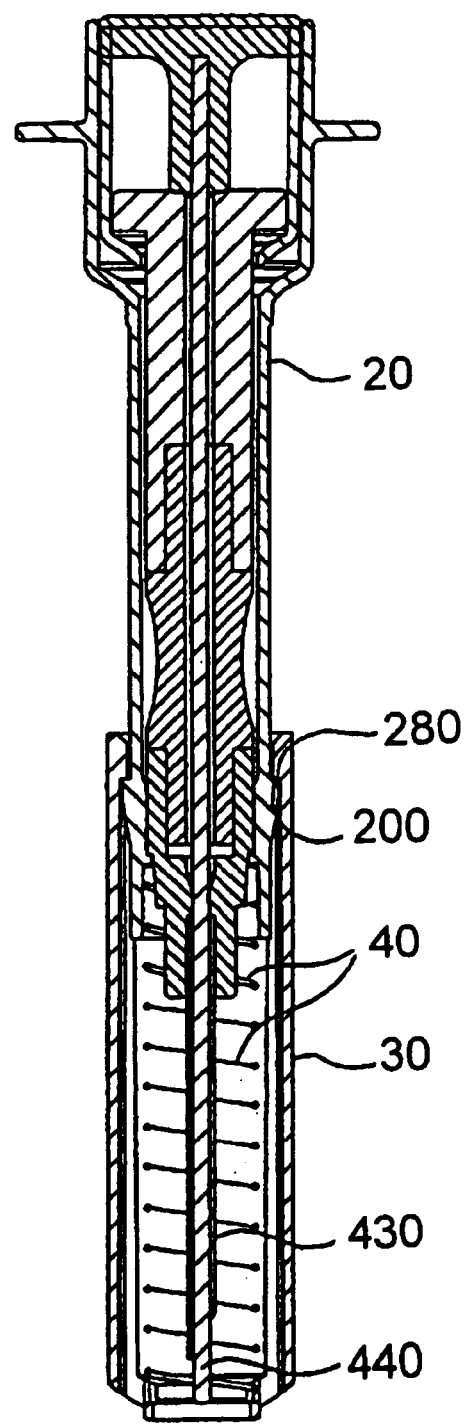
Figure 24:
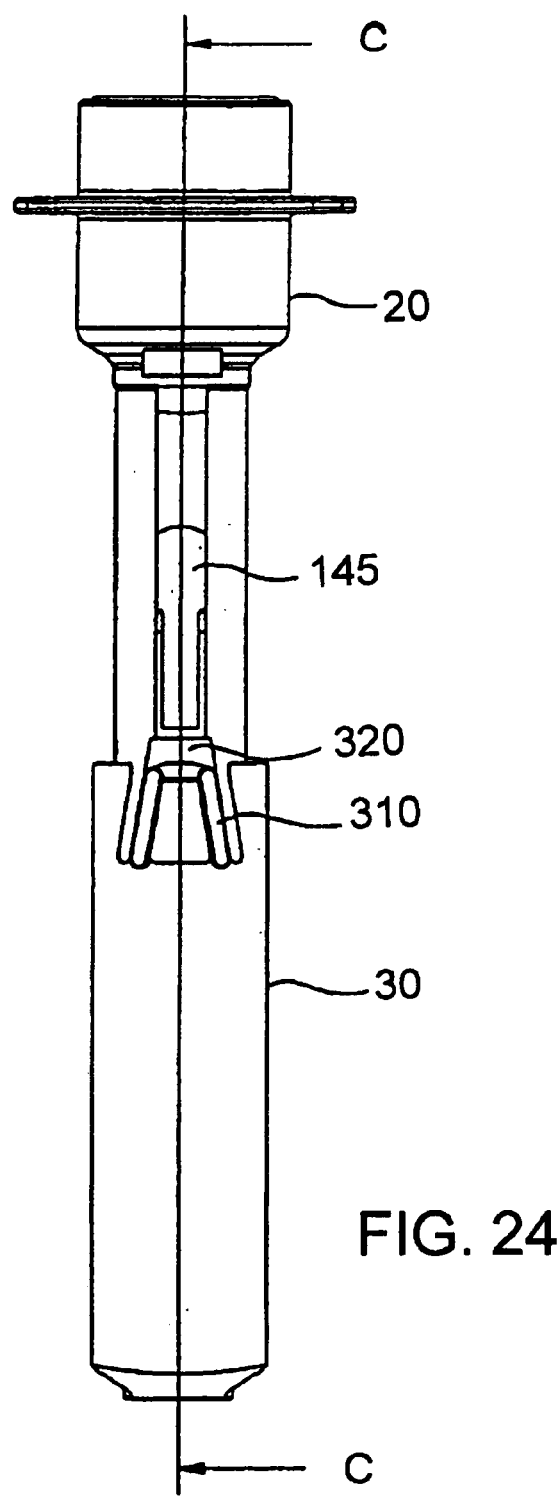
Figure 25:
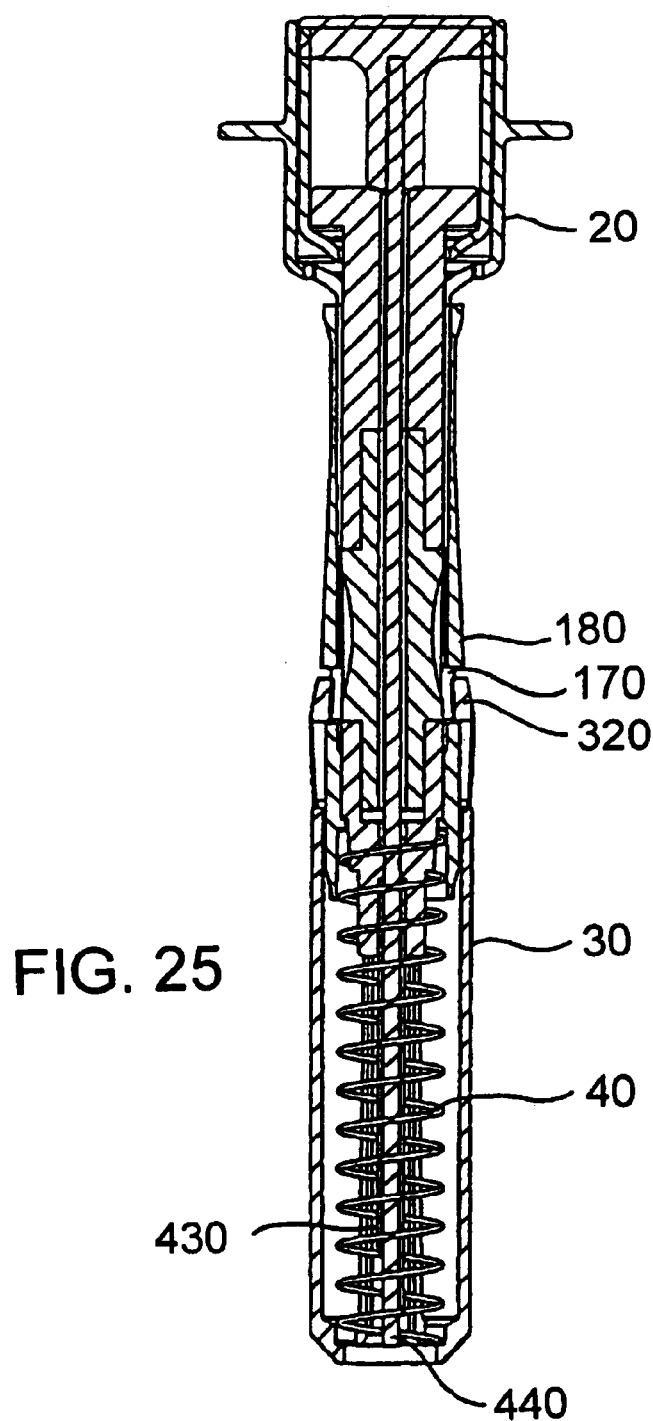
Figure 26:
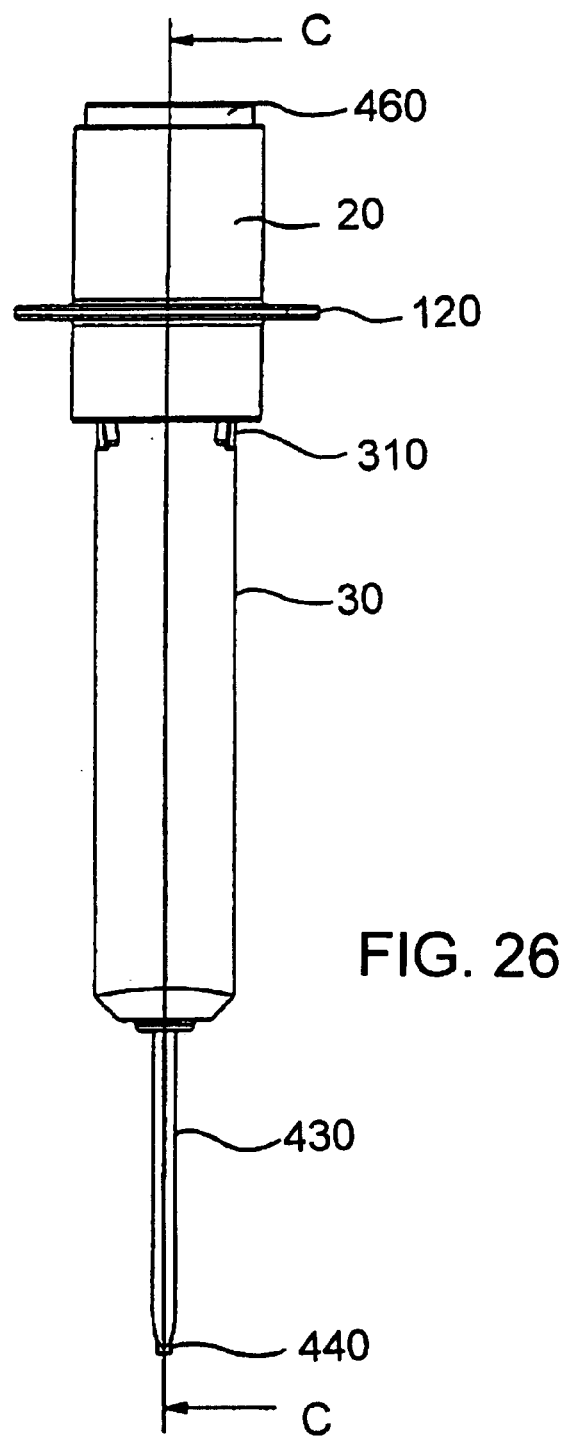
Figure 27:
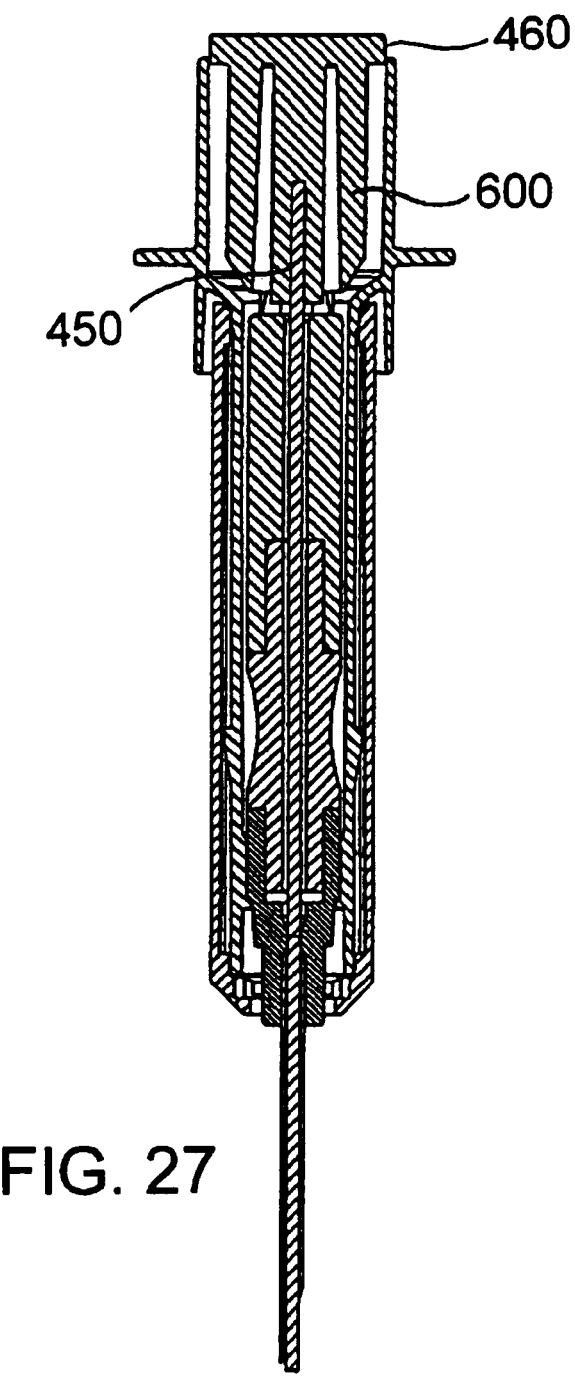
Figure 28:
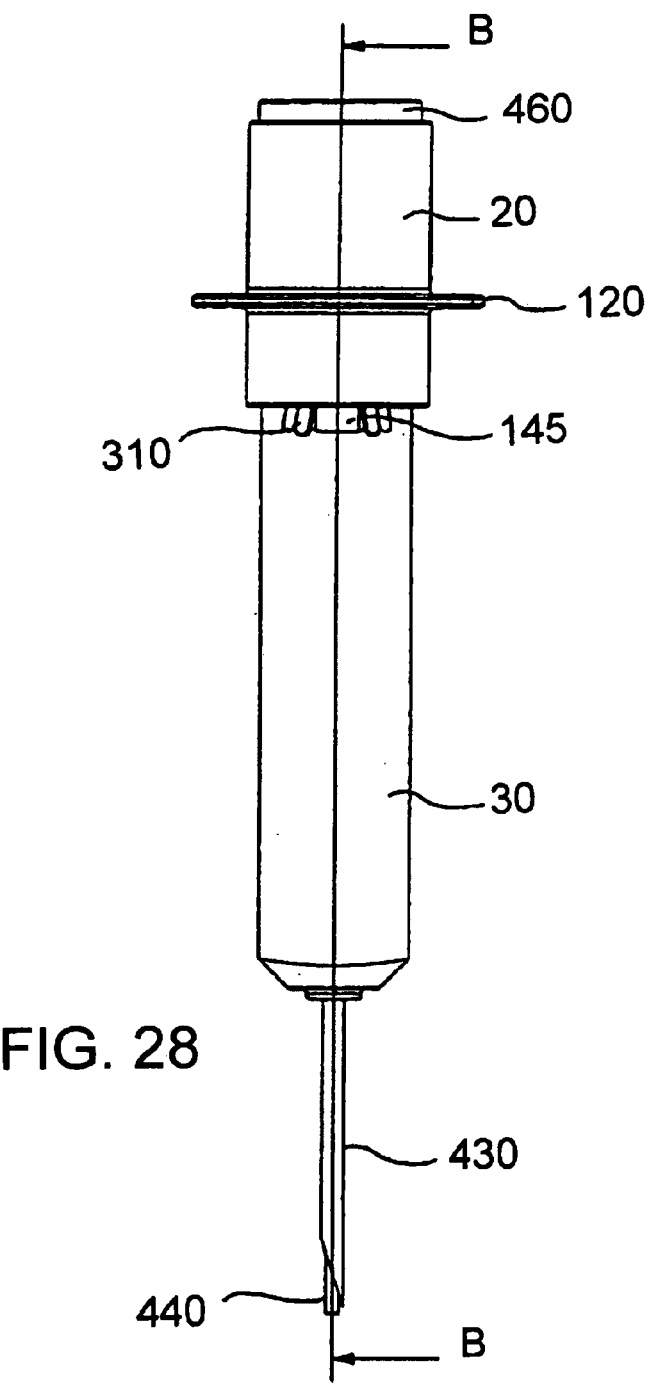
Figure 29:
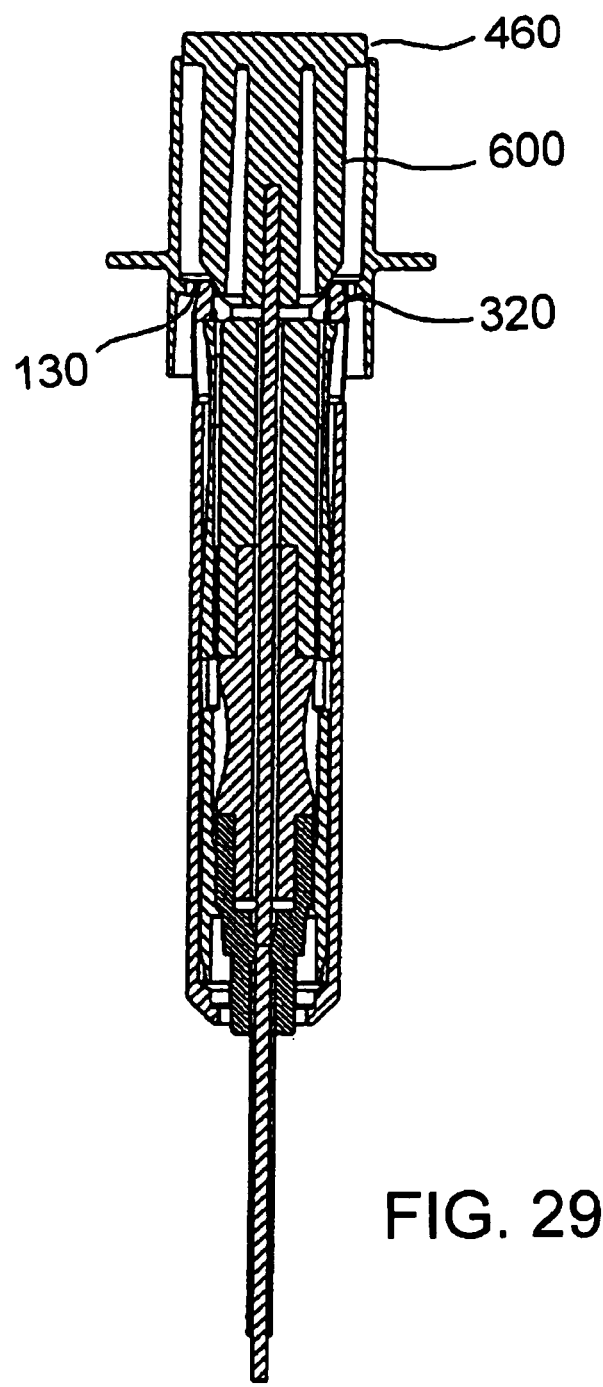
Figure 30:
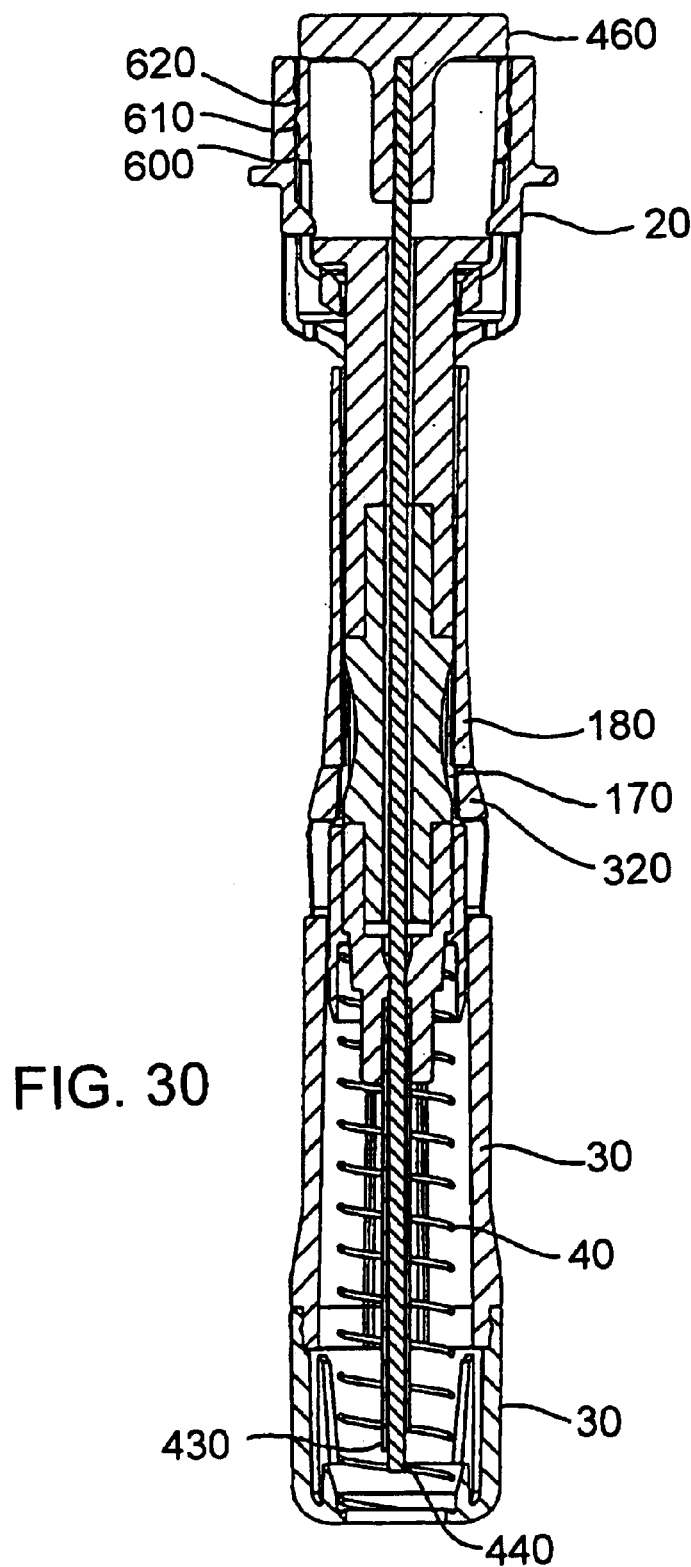
Figure 31:
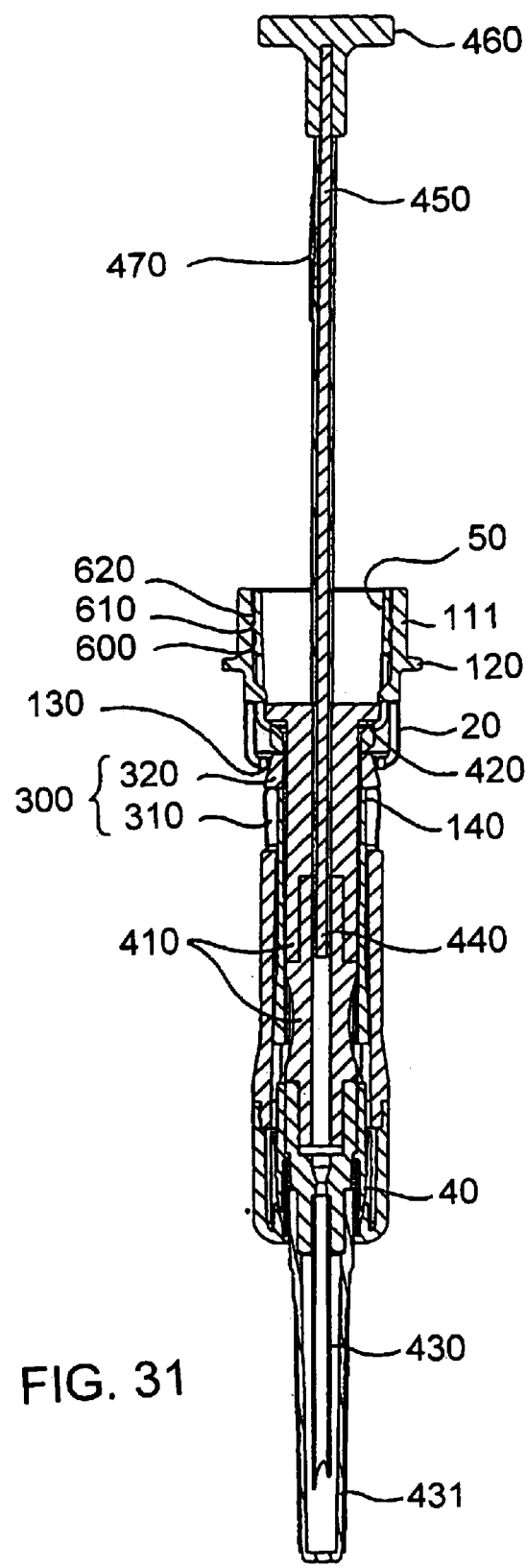

FIG. 15*a* shows an enlarged view of circled area L of FIG. 15;

FIG. 16 shows a cut-away view along line G—G of FIG. 15;

FIG. 17 shows a side view of a trigger;

FIG. 18 shows a section on line F—F of FIG. 17;

FIG. 19 shows a top view of the trigger of FIG. 17;

FIG. 20 shows a perspective view of a safety shield and syringe arrangement, shown in more detail in FIGS. 21 30 and 31;

FIG. 21 shows a partially cut away perspective view of a safety shield and syringe arrangement of the present invention, the outer shield being in its extended position;

FIG. 22 shows a front view of the arrangement of FIG. 1 in the extended position;

FIG. 23 shows a section on line B—B of FIG. 22;

FIG. 24 shows a side view of the arrangement of FIG. 1 in the extended position;

FIG. 25 shows a section on line C—C of FIG. 24;

FIG. 26 shows a front view of a second safety shield and syringe arrangement prior to extension of the safety shield;

FIG. 27 shows a section on line C—C of FIG. 26;

FIG. 28 shows a side view of the arrangement of FIG. 26;

FIG. 29 shows a section on line B—B of FIG. 28;

FIG. 30 shows a section through an alternate embodiment of the present invention, generally equivalent to that shown in FIG. 25; and FIG. 31 shows an alternate section through the arrangement of FIG. 30, generally equivalent to that shown in FIG. 4.

EXAMPLE 1

In a first embodiment, the safety shield and syringe arrangement 10 of the present invention comprises inner holder 20, outer shield 30, metal coil spring 40, trigger 50 and syringe 60.

Inner holder 20 is constructed from Eastar (RTM) copolyester DN003 (Eastmnan Chemical Company) and is of an elongate, generally cylindrical shape, defining enclosure 70, and has inner holder proximal portion 80 and inner holder distal portion 90 and ends 100,110 defining end openings. Proximal portion 80 widens towards end 100 to form mouth 111 which in use is gripped by the hand of a user. Mouth 111 is substantially rigid such that pressure exerted by a user does not reduce its diameter and hinder the operation of the safety shield arrangement 10 and thus extension of outer shield 30. Mouth 111 has radially outwardly extending flange 120 which in use acts as a finger grip, allowing easy manipulation of arrangement 10 by a user. Located at the distal end of mouth 111 are two first openings 130 radially opposite one another, and having distal surfaces defined by two first frustoconical portions 140 providing upper abutment surfaces 150 and lower inclined surfaces 160. Extending axially distal from first frustoconical portions 140 are first grooves 145. Located in distal portion 90, axially distal from first openings 130, are two first indentations 170 with two deflectable tongues 180 extending into them in a proximal to distal direction. The distal ends 181 of tongues 180 extend radially outwards from proximal ends 182.

Axially rotated 90 degrees from first openings 130, first frustoconical portions 140 and first indentations 170 and extending distally are two second grooves 185. Located in distal portion 90 are two detents comprising two outwardly extending second frustoconical portions 190, having upper abutment surfaces 200 and lower inclined surfaces 210. Radially inwards of second frustoconical portions 190 is radially inwardly extending collar 220 which (see below) engages syringe 60. Axially distal of collar 220 is radially inwardly extending distal flange 230 having upper and lower abutment surfaces 231,232.

Outer shield 30, also constructed from Eastar copolyester DN003, is of a shape which matches that of inner holder 20 such that it is axially slidable over inner holder 20. Outer shield 30 has proximal and distal portions 240,250 and proximal and distal ends 260,270. Proximal end 260 is provided with two radially opposite inwardly extending flanges providing abutment surfaces 280 having axially extending inclined side walls 290. Abutment surfaces 280 and side walls 290 are shaped such that they are able to cover second frustoconical portions 190 with a tight fit. Proximal end 260 is also provided with two stop members 300 axially rotated 90 degrees from abutment surfaces 280. Stop members 300 comprise deflectable arms 310 generally having the shape of the perimeter of a bilaterally symmetrical trapezoid, and heads 320. The distal end of arms 310 extends inwardly and moving axially, arms 310 extend outwardly. Heads 320 extend inwardly of the proximal end of arms 310 and provide proximal abutment surfaces 330. Distal end 270 is provided with generally annular protrusion 340 providing inclined abutment surface 350, axially distal to which extends second distal detent 370 having distal abutment surface 360.

Trigger 50 is of a generally cylindrical shape, having proximal and distal ends 380,390 and is designed to fit into mouth 111 of inner holder 20 such that it is axially slidable within mouth 111. Distal end 390 has inwardly curving neck 400.

Syringe 60 comprises generally cylindrical barrel 410 containing solid medicament formulation (not shown) having flange 420 at its proximal end and needle 430 and removable needle cover 431 at its distal end. Piston 440 is slidably positioned within barrel 410. Plunger rod 450 is engaged at one end with piston 440 and at the other end has a flange providing thumb push 460. Safety clip 470 is removably secured to the portion of plunger rod 450 exposed from barrel 410l and prevents movement of plunger rod 450.

The safety shield and syringe arrangement is constructed by first placing metal coil spring 40 within outer shield 30 such that it contacts abutment surface 360 of distal flange 370. End 110 of inner holder 20 is then gripped and slid within proximal end 260 of outer shield and slid towards distal end 270. Arms 310 and heads 320 of stop members 300 are deflected outwards as they pass over inclined surfaces 160 of frustoconical portions 140 until they have been slid past frustoconical portions 140, at which point they snap inwardly such that abutment surfaces 150,330 are opposite one another. Further sliding of inner holder 20 is prevented by end 110 contacting inclined abutment surface 350 of outer shield 30. The sliding of inner holder 20 within outer shield 30 causes spring 40 to be compressed between abutment surface 360 of outer shield 30 and lower abutment surface 232 of inner holder 20. Releasing the grip on inner holder 20 allows spring 40 to expand slightly, urging apart inner holder 20 and outer shield 30, and opposing abutment surfaces 150,330 engage one another and prevent further relative movement of inner holder 20 and outer shield 30. The outer shield is now engaged in a retracted position.

The arrangement of arms 310 and heads 320 of stop members 300 is such that the centre of the pivotal axis of arms 310 is radially inwards of the area of contact of abutment surfaces 150,330. In contrast with prior art devices whose holder and shield parts may be disengaged by exerting sufficient force, this means that attempting to pull apart (i.e. disengage) inner holder 20 and outer shield 30 causes stop members 300 to engage inner holder 20 more substantially.

Trigger 50 is then slid into mouth 111 of inner holder 20 such that neck 400 contacts heads 320.

Syringe 60 is then inserted, needle 430 first, into mouth 111 of inner holder 20 and slid towards end 110 such that needle 430 and needle cover 431 protrude from end 110. Insertion is halted when barrel 410 contacts upper abutment surface 231 of distal flange 230. Proximal and distal ends of barrel 410 of syringe 60 are constructed from high density polythene and an interference fit is formed with collar 220 such that it cannot be readily removed from inner holder 20 without the exertion of substantial force. Flange 420 prevents trigger 50 from being removed from mouth 111, but does not exert any force upon trigger 50 and does not cause and movement of trigger 50 which may result in the disengagement of inner holder 20 and outer shield 30.

In use, safety clip 470 is removed from plunger rod 450, and needle cover 431 is also removed. Needle 430 is inserted into a patient (not shown) and thumb push 460 depressed to slide piston 440 through barrel 410 and expel solid medicament formulation (not shown) from needle 430 and to cause piston 440 to extend from needle 430. Simultaneously (i.e. not as part of a separate step), thumb push 460 enters mouth 111 and contacts trigger 50, causing it to move axially. This axial movement of trigger 50 is hindered by heads 320, but curved neck 400 deflects heads 320 outwardly as trigger 50 moves axially. Sufficient axial movement of trigger 50 and thus outwards movement of heads 320 causes opposing abutment surfaces 150,330 to become disengaged, allowing axial movement of outer shield 30.

Spring 40 urges apart inner holder 20 and outer shield 30 and as needle 430 is removed from patient 480 outer shield 30 is caused to slide over inner holder 20, covering needle 430 and preventing any possible needle sticks. During the sliding step, rotation of inner holder 20 and outer shield 30 relative to one another is prevented by grooves 145,185 guiding heads 320 of stop members 300 and second frustoconical portions 190 respectively. As needle 430 is fully removed from patient 480 heads 320 pass over inclined tongues 180 and lockably snap into first indentations 170, preventing further axial movement of inner holder 20 and outer shield 30. Simultaneously, abutment surfaces 280 and side walls 290 slide over second frustoconical portions 190 with a tight fit, abutment surfaces 280 contacting upper abutment surfaces 200, and preventing any further extension as an additional safety feature. The outer shield is now locked in an extended position. The entire operation of the safety shield and syringe arrangement 10 of the present invention can be readily achieved by a person using a single hand.

EXAMPLE 2

A second embodiment is as Example 1 except that syringe barrel 410 does not have flange 420, and trigger 50 is not held in mouth 111, instead being replaced by axial extension 600 of thumb push 460. This configuration minimises the possibility of accidentally causing disengagement of opposing abutment surfaces 150,330 whilst placing syringe 60 in inner holder 20, or of otherwise accidentally causing disengagement of opposing abutment surfaces 150,330. Absent flange 420, it is also possible to reduce the diameter of mouth 111 and therefore either reduce the overall dimensions of inner holder 20 or to extend flange 120 to allow for further improved gripping by a user.

EXAMPLE 3

A third embodiment is identical to Example 1 except that mouth 111 is provided with deflectable frustoconical portions 500 (not shown) having upper (proximal) inclined surfaces 501 (not shown) and lower (distal) abutment surfaces 502 (not shown) substantially perpendicular to the axis of the inner holder. In use, as thumb push 460 enters mouth 111 (and the solid medicament formulation is expelled from needle 430 and piston 440 extends from needle 430) it deflects frustoconical portions 500 and passes beyond them, at which point they return to their original shape and present abutment surfaces 502 which oppose thumb push 460, preventing its removal from mouth 111. This means that piston 440 is locked in position extending from needle 430 such that even if outer shield 30 is removed or damaged such that needle 430 is exposed, needle sticks are substantially prevented.

EXAMPLE 4

An alternative embodiment having altered (generally narrower than those shown in other Figures) dimensions is shown in FIGS. 30, 31, 20 and 21. In particular, inner holder 20 has a length of about 68 mm and a diameter of about 10 mm in the proximal portion which is covered by outer shield 30, and having a narrowed flange 120. Notably, outer shield 30 is of a two-part construction.

Trigger 50 is also provided with first and second curved protrusions 600, 610 extending radially outwards around the whole of its circumference, trigger 50 (and/or mouth 111) being sufficiently elastically deformable to allow them to be forced past corresponding third curved protrusion 620 which extends radially inwards around the whole of the circumference of mouth 111. When the apparatus of the present invention is constructed, trigger 50 is inserted into mouth 111 of inner holder 20 and first curved protrusion 600 abuts third curved protrusion 620. Sufficient downwards force can readily be applied to trigger 50 to cause it to elastically deform to allow first curved protrusion 600 to pass over third curved protrusion 620. As trigger 50 is pushed further downwards, second curved protrusion 610 abuts third curved protrusion 620. Sufficient downwards force is then applied to trigger 50 to cause it to elastically deform to allow second curved protrusion 610 to pass over third curved protrusion 620. Trigger 50 is thus fully inserted as shown in FIGS. 30 and 31. Although downwards force can be readily applied to trigger 50 to insert it into mouth 111, once in place it is extremely difficult for a person to apply sufficient upwards force to trigger 50 to remove it from mouth 50, and may be considered to be permanently located within mouth 111.

With this two-stage insertion of trigger 50, devices of the present invention are stored and shipped with inner holder 20, outer shield 30 and spring 40 engaged with one another and trigger 50 inserted into mouth 111 of inner holder 20 such that third curved protrusion 620 is located between first and second curved protrusions 600 and 610. Syringe 60 can be inserted into mouth 111 and engage inner holder 20 without contacting trigger 50. Even if trigger 50 is accidentally contacted whilst syringe 60 is being inserted, second curved protrusion 610 hinders it from moving beyond third curved protrusion 620 and therefore prevents it from disengaging stop members 300 from first openings 130. When syringe 60 has been fully inserted then sufficient force can be applied to trigger 50 to push second curved protrusion 610 past third curved protrusion 620. Syringe arrangement 10 is now ready for use.

Depending on the construction and deformability of mouth 111 and thumb push 460, as well as the dimensions of thumb push 460, it is possible for a protrusion extending radially inwards around the whole of the circumference of mouth 111 to be used to prevent the removal of thumb push 460 from mouth 111.

What is claimed is:

1. An automatically operable safety shield system for use with a syringe, said safety shield system comprising:

an inner holder having proximal and distal portions and defining an enclosure into which said syringe may be inserted;

an outer shield having proximal and distal portions, mounted outwards from said inner holder and being axially movable relative to said inner holder between retracted and extended positions;

a spring positioned between a first detent on said inner holder and a second detent on said outer shield, and urging said outer shield to its extended position;

said inner holder having at least one first opening and said outer shield having at least one first stop member, said first stop member being engageable with said first opening when said outer shield is in said retracted position;

said inner holder having distal to said first opening at least one first indentation, said first stop member being engageable with said first indentation when said outer shield is in said extended position; and a trigger positioned within said inner holder and axially movable relative to said inner holder such that it can contact said first stop member when it is engaged with said first opening and disengage said first stop member from said first opening, allowing said spring to move said outer shield to said extended position.

2. An automatically operable safety shield system according to claim 1, said first and second detents being positioned, respectively, on said distal portions of said inner holder and outer shield.

3. An automatically operable safety shield system according to either one of claims 1 or 2, additionally comprising a syringe comprising a barrel, a needle, a piston and a plunger rod movable within said barrel, said plunger rod having a protrusion, said syringe being operationally coupled to said trigger such that movement of said plunger rod protrusion to contact said trigger causes disengagement of said first stop member from said first opening, allowing said spring to move said outer shield to said extended position.

4. An automatically operable safety shield system, comprising:

a syringe comprising a barrel, a needle, a piston and a plunger rod movable within said barrel, said plunger rod having a protrusion;

an inner holder having proximal and distal portions and defining an enclosure into which said syringe may be inserted;

an outer shield having proximal and distal portions, mounted outwards from said inner holder and being axially movable relative to said inner holder between retracted and extended positions;

a spring positioned between a first distal detent on said innerholder and a second distal detent on said outer shield, and urging said outer shield to said extended position;

said inner holder having at least one first opening and said outer shield having at least one first stop member, said first stop member being engageable with said first opening when said outer shield is in said retracted position;

said inner holder having distal to said first opening at least one first indentation, said first stop member being engageable with said first indentation when said outer shield is in said extended position; and said syringe being operationally coupled to said inner holder and outer shield such that axial movement of said plunger rod protrusion relative to said inner holder causes said plunger rod protrusion to contact said first stop member when it is engaged with said first opening and disengage said first stop member from said first opening, allowing said spring to move said outer shield to said extended position.

5. An automatically operable safety shield system according to claim 4, said syringe being provided with a safety clip removably secured to the portion of said plunger rod exposed from said barrel such that movement of said plunger rod is prevented when said safety clip is secured to said plunger rod.

6. An automatically operable safety shield system according to claim 5, said outer shield and inner holder having, respectively, proximal and distal abutment surfaces in opposing relationship to one another, which can engage one another to prevent movement of said outer shield beyond its extended position.

7. An automatically operable safety shield system according to claim 6, said inner holder and outer shield being of a generally cylindrical shape and having a cross-section selected from the group consisting of circular and elliptical.

8. An automatically operable safety shield system according to claim 7, said generally cylindrically shape being a tapered cylindrical shape.

9. An automatically operable safety shield system according to claim 7, at least one of said inner holder and outer shield having guide means for axial movement to prevent relative rotation of said inner holder and outer shield.

10. An automatically operable safety shield system according to claim 9, said inner holder having corresponding to said first stop member a groove along which said first stop member is slidable.

11. An automatically operable safety shield system according to claim 6, at least one of said inner holder and outer shield having guide means for axial movement to prevent relative rotation of said inner holder and outer shield.

12. An automatically operable safety shield system according to claim 6, said inner holder having corresponding to said first stop member a groove along which said first stop member is slidable.

13. An automatically operable safety shield system according to claims 10, 11 or 12, said outer shield having corresponding to each of said distal abutment surfaces a groove along which said distal abutment surface is slidable.

14. An automatically operable safety shield system according to claim 12, said inner holder having an inner holder detent comprising a radially inwardly extending distal flange having an upper abutment surface which is contacted by said syringe, preventing further distal movement of said syringe in said inner holder.

15. An automatically operable safety shield system according to claim 14, said inner holder having syringe engagement means for engaging and retaining said syringe.

16. An automatically operable safety shield system according to claim 15, said inner holder having at its proximal end at least one radially extending protrusion usable as a finger grip.

17. An automaticahy operable safety shield system according to claim 16, said at least one radially extending protrusion at said inner holder proximal end being a flange extending around the whole of the circumference of said inner holder.

18. An automatically operable safety shield system according to claim 17, said outer shield not having at its proximal end any radially extending protrusions usable as a finger grip.

19. An automatically operable safety shield system according to claim 18, said inner holder additionally comprising plunger rod retaining means which prevent backwards movement of said plunger rod when it is at least almost at its forwardmost position.

20. An automatically operable safety shield system according to claim 19, said first stop member extending first outwardly and then inwardly from said outer shield such that said first stop member, when engaged with said first opening, has the centre of its pivotal axis inwards of the point of engagement with said first opening.

* * * * *

UNITED STATES PATENT AND TRADEMARK OFFICE
CERTIFICATE OF CORRECTION

| | | |
|---|---|---|
| PATENT NO. | : 7,118,552 B2 | Page 1 of 1 |
| APPLICATION NO. | : 09/936859 | |
| DATED | : October 10, 2006 | |
| INVENTOR(S) | : Derek Shaw and Brian Law | |

It is certified that error appears in the above-identified patent and that said Letters Patent is hereby corrected as shown below:

Title page, item 56
In the References Cited section, the following references are missing:

--US 4,758,231
US 4,062,353--

US 5,201,720, "Boergia" should read --Borgia--

In the Abstract, line 2, after "an" insert --inner--.

In the Abstract, line 6, after "holder" insert --and--.

In the Abstract, line 17, after "position" insert --and a trigger positioned within the inner holder and axially movable relative to the inner holder such that it can contact the first stop member from the first opening, allowing the spring to move the outer shield to the extended position.--

Col. 16, claim 14, line 29, "claim 12" should be --claim 13--

Col. 16, claim 17, line 41, "automaticahy" should be --automatically--

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,118,552 B2
APPLICATION NO. : 09/936859
DATED : October 10, 2006
INVENTOR(S) : Derek Shaw and Brian Law It is certified that error appears in the above-identified patent and that said Letters Patent is hereby corrected as shown below:

On Title Page Item 56

In the References Cited section, the following reference is missing, please add:

US 5,059,180

Signed and Sealed this

Third Day of June, 2008

JON W. DUDAS
*Director of the United States Patent and Trademark Office*